(12) United States Patent
Kohls et al.

(10) Patent No.: US 12,239,843 B2
(45) Date of Patent: Mar. 4, 2025

(54) SYSTEM AND METHOD FOR OPERATING A PLASMA JET CONFIGURATION

(71) Applicant: LEIBNIZ-INSTITUT FÜR PLASMAFORSCHUNG UND TECHNOLOGIE E.V., Greifswald (DE)

(72) Inventors: Rayk Kohls, Dersekow (DE); Klaus-Dieter Weltmann, Ostseebad Binz (DE); Philipp Turski, Greifswald (DE); Norbert Lembke, Greifswald (DE); Torsten Gerling, Greifswald (DE); Laura Vilardell Scholten, Greifswald (DE); Stefan Horn, Loissin (DE)

(73) Assignee: LEIBNIZ-INSTITUT FÜR PLASMAFORSCHUNG UND TECHNOLOGIE E.V., Greifswald (DE)

( * ) Notice: Subject to any disclaimer, the term of this patent is extended or adjusted under 35 U.S.C. 154(b) by 0 days.

(21) Appl. No.: 17/766,263

(22) PCT Filed: Oct. 5, 2020

(86) PCT No.: PCT/EP2020/077857
§ 371 (c)(1),
(2) Date: Apr. 4, 2022

(87) PCT Pub. No.: WO2021/064242
PCT Pub. Date: Apr. 8, 2021

(65) Prior Publication Data
US 2024/0050760 A1    Feb. 15, 2024

(30) Foreign Application Priority Data

Oct. 4, 2019  (EP) ..................................... 19201495
Mar. 5, 2020  (EP) ..................................... 20161148

(51) Int. Cl.
*A61N 1/44*  (2006.01)
*H05H 1/46*  (2006.01)

(52) U.S. Cl.
CPC ............... *A61N 1/44* (2013.01); *H05H 1/461* (2021.05); *H05H 2245/34* (2021.05)

(58) Field of Classification Search
None
See application file for complete search history.

(56) References Cited

U.S. PATENT DOCUMENTS 8,963,044 B2    2/2015  Kim et al.
2014/0162338 A1  6/2014  Schaefer et al.
(Continued)

FOREIGN PATENT DOCUMENTS

JP    2006244938    9/2006
JP    2007188690    7/2007
(Continued)

*Primary Examiner* — Ashok Patel
(74) *Attorney, Agent, or Firm* — JMB Davis Ben-David

(57) ABSTRACT

The invention relates to a system (1) for generating and controlling a non-thermal atmospheric pressure plasma, comprising: —a discharge space (10) into which a working gas can be introduced via a first opening (12), wherein a plasma (5) can be generated in the discharge space (10), wherein the discharge space (10) has a second opening (14), so that the plasma (5, 6) can exit from the discharge space (10) through this second opening (14) and —at least one high-voltage electrode (20) for generating an electromagnetic field for generating a plasma (5) in the discharge space (10). The plasma (5, 6) exiting through the second opening (14) is controlled by a throughflow controller (40) of the system (1), which throughflow controller (40) is designed to adjust a volume flow (60) of the working gas through the first opening (12) from a working gas source (50) into the discharge space (10). In this case, the throughflow controller (40) is further designed to assume at least a first state and a (Continued)

second state, wherein in the first state no working gas is supplied from the working gas source (50) to the discharge space (10), so that no plasma (5) exits from the second opening (14) even when there is a generated electromagnetic field in the discharge space (10), and wherein in the second state the working gas is supplied from the working gas source (50) to the discharge space (10), a plasma (5) is generated in the discharge space (10) and the plasma (5, 6) exits from the second opening (14).

14 Claims, 15 Drawing Sheets

(56) References Cited

U.S. PATENT DOCUMENTS

| 2018/0322963 A1* | 11/2018 | Wong | H05H 1/16 |
|---|---|---|---|
| 2019/0133669 A1 | 5/2019 | Sheperak | |

FOREIGN PATENT DOCUMENTS

| WO | 2009036579 | 3/2009 |
|---|---|---|
| WO | 2009060213 | 5/2009 |
| WO | 2009146432 | 12/2009 |
| WO | 20110053599 | 5/2011 |
| WO | 2019093388 | 5/2019 |

\* cited by examiner

SYSTEM AND METHOD FOR OPERATING A PLASMA JET CONFIGURATION

CROSS-REFERENCE TO RELATED APPLICATIONS

This is the U.S. National Stage of International Patent Application No. PCT/EP2020/077857 filed on Oct. 5, 2020, which claims priority to European Patent Application No. 19201495.9 filed on Oct. 4, 2019 and European Patent Application No. 20161148.0 filed on Mar. 5, 2020.

The invention relates to a system and a method for generating and controlling a non-thermal atmospheric pressure plasma.

Non-thermal atmospheric pressure plasmas are used, among other things, for medical purposes. This field of application is also known as "plasma medicine".

Non-thermal atmospheric pressure plasma is also referred to as plasma in the following of the present application.

A plasma is understood to be a gas with a proportion of free electrons, radicals, ions and neutral particles. Depending on the type of working gas, reactive species are generated by the plasma, for example reactive oxygen species such as ozone ($O_3$). Reactive species can have an antimicrobial effect. Therefore, treatment with a plasma can support wound healing.

A plasma is generatable in a plasma jet arrangement, for example. In this case, a plasma is generatable in a discharge space in an electromagnetic field, which is transported out of the device, particularly the discharge space, with a gas flow in the form of a plasma jet.

Plasma jet arrangements are known in the prior art (Winter, J., Brandenburg, R., and Weltermann, K.-D. (2015), "Atmospheric pressure plasma jets: an overview of devices and new directions", Plasma Sources Sci. Technol., 24, 064001). Such arrangements are particularly suitable for treatment of a small region.

The control of the plasma or the plasma jet of a plasma jet arrangement takes place via an electrical or electronic control of the respective applied electromagnetic field. For example, the electromagnetic field is brought to a standstill by means of the electrical or electronic control, so that no more plasma is generated in the discharge space and thus no plasma exits the discharge space as a plasma jet. A new electromagnetic field is generated so that a plasma jet is generatable again.

For treatment of larger areas, for example for wound healing in burn victims, individual plasma jet arrangements are only insufficiently suitable, as they emit a focused plasma jet and therefore provide for spot treatment.

Various solutions are known from the prior art to enable large-area plasma treatment. Document US 2009/018 86 26 A1 discloses an arrangement in which a plurality of electrodes are arranged in a common dielectric container. The document US 2004/012 38 03 A1 describes an arrangement in which a gas from a plurality of nozzles is continuously introduced into the space between two electrodes and in addition another gas can be supplied to this space in pulses.

A plurality of individual plasma jets arranged side by side is also referred to as plasma jet arrays in the context of this application. In the case of simultaneous operation of the individual plasma jet arrangements of the plasma jet array, the respective electromagnetic fields of the individual plasma jet arrangements would influence each other without suitable shielding of the fields. Therefore, a high effort for a suitable shielding is necessary, so that such an arrangement of a plasma jet array is very complex and cost-intensive in manufacturing.

For simple and user-friendly use, plasma jet arrangements are of interest whose generated plasmas and/or exiting plasma jets are easy to control, for example, can be switched on and/or off in a simple manner. Furthermore, plasma jet arrays that are easy to control and inexpensive to manufacture are of interest.

These objectives are solved by the system according to claim 1 as well as the method according to claim 13. Advantageous embodiments of the device are given in the subclaims. These and further embodiments are described below.

A first aspect of the invention relates to a system for generating and controlling a non-thermal atmospheric pressure plasma. The system has a discharge space into which a working gas is introducable via a first opening. A plasma is generatable in the discharge space, particularly from the introduced working gas. The discharge space has a second opening, so that the plasma can exit the discharge space through this second opening.

The system has at least one high-voltage electrode for generating an electromagnetic field for generating a plasma, in particular for generating a plasma ignited from the working gas, in the discharge space.

The plasma exiting through the second opening is controlled by a flow controller of the system, which is formed to set a volume flow of the working gas through the first opening from a working gas source into the discharge space. The flow controller is further formed to adopt at least a first state and a second state. In the first state, no working gas is supplied from the working gas source to the discharge space, so that even with generated, in particular generated by the high-voltage electrode, electromagnetic field in the discharge space no plasma exits from the second opening. In other words, this means that in the first state, no working gas is supplied from the working gas source to the discharge space, so that no plasma exits from the second opening even with existing electromagnetic field in the discharge space. In the second state, the working gas from the working gas source is supplied to the discharge space. A plasma is generated in the discharge space and the plasma exits the second opening. In particular, the plasma is generated from the volume flow of the working gas supplied through the first opening immediately by the electromagnetic field generated by the high voltage electrode. Therefore, controlling the volume flow by means of the flow controller allows direct and immediate control of a plasma jet exiting at the second opening, and eliminates the need for continuous generation of a primary plasma to ignite a secondary plasma.

This type of control represents a massive technical simplification of the system, particularly since the generation and permanent maintenance of a primary plasma is not required in the discharge space.

The invention describes how a modulation of the volume flow of the working gas can be achieved in an advantageous manner with the aid of a flow controller and thus permits, in particular by means of a flow controller that can be controlled quickly, a precise, i.e. time-resolved and location-resolved (in the case of its plurality of discharge spaces) dosing of the volume flow. The modulation of the volume flow relates in particular not only to a simple "on" and "off" switching, but also to a targeted control of a plasma jet exiting at the second opening via the volume flow of the working gas. The same applies to finely dosable admixing to the working gas.

The advantages of the invention are particularly apparent in a multijet arrangement, i.e. a system according to the invention with a large number of discharge spaces.

If electrical energy is used to operate/modulate a plasma jet, it is always accompanied by electromagnetic interference, on the one hand from the control of the high-voltage source and on the other hand from the plasma itself. In an array of several plasma jets, there will always be mutual interference between them, which will affect the proper operation and setting of the desired/required plasma parameters. One cannot now reduce, let alone eliminate, this negative influence of electromagnetic interference without considerable technical effort. The approach of the invention to selectively regulate the supply and optionally the composition of the working gas allows for a simple and economically advantageous effort. On the one hand, the technical complexity in the electronic control of the high voltage generation is reduced, and on the other hand, a fluid dynamic complexity is added. However, the overall complexity of the system is still reduced and more problems are solved, especially with regard to the arrays.

A non-thermal plasma, in the context of this application, is also referred to as a low-temperature plasma or a cold plasma. The plasma that is transported by a gas flow, in particular the volume flow of the working gas, out of the discharge space through the second opening is also referred to as a plasma jet or plasma beam in the context of the document.

The discharge space may be delimited by a wall. The wall may delimit the first opening. According to the invention, the wall may delimit the second opening. The wall may be formed as a dielectric.

The discharge space comprises in particular the volume in which the plasma is generatable.

An electromagnetic field is generatable at the high-voltage electrode when voltage is applied. The generated electromagnetic field is also referred to as the existing electromagnetic field in this application. With the aid of the generated or existing electromagnetic field, a non-thermal atmospheric pressure plasma is generatable.

Plasmas can also be generated by means of lasers or ion beams. However, the parameters of the plasma, such as temperature, leakage current or species generation, are comparatively difficult to control and, compared to the principle of the invention, involve increased technical effort.

One embodiment provides that the high voltage electrode is arranged within the discharge space.

The discharge space can be fluidically connected to a working gas source via the first opening. This means that working gas from the working gas source is introducable into the discharge space through the first opening.

A working gas may comprise or be any of the following gases: Hydrogen, argon, helium, nitrogen, oxygen, neon, krypton, or carbon dioxide. The working gas may be a gas mixture comprising at least one of the following gases: Hydrogen, argon, helium, nitrogen, oxygen, neon, krypton, or carbon dioxide. In particular, the working gas may comprise argon or be argon.

The flow controller can adopt at least a first and a second state. In the first state of the flow controller, the flow controller is configured so that no working gas is introduced into the discharge space. In other words, in the second state, this means that a gas supply (in particular the supply of the working gas) to the discharge space is interrupted. No working gas flows from the first opening through the discharge space towards the second opening. Further, no working gas flows from the first opening toward the second opening and out of the discharge space. There is no volume flow of the working gas in the discharge space. No plasma is transported out of the second opening in the form of a plasma jet with the volume flow.

When no working gas is introduced into the discharge space, so that no plasma jet exits the discharge space, no working gas exits the discharge space. The consumption of the working gas is thus advantageously reduced compared to a prior art device in which working gas continuously flows through the discharge space and out of the discharge space.

The system may be configured such that no plasma is generated in the discharge space in the first state.

In the second state of the flow controller, it is formed such that working gas is introduced into the discharge space. In particular, working gas is introduced in such a way that it flows through the first opening into the discharge space and flows through the discharge space in the direction of the second opening. In particular, the introduced working gas flows from the first opening toward the second opening and out of the second opening out of the discharge space.

Due to the volume flow of the working gas, the plasma generated in the discharge space exits the discharge space as a plasma jet through the second opening.

By controlling the flow controller, it is possible to set whether plasma exits the discharge space as a plasma jet or not. In other words, this means that with the system according to the invention, fluid dynamic control of the ejection of the plasma from the discharge space is achieved. This means that fluid dynamic control of the plasma jet can take place. Thus, in a simple way, without any control or regulation of the electromagnetic field, the plasma jet can be controlled, in particular it can be controlled whether a plasma jet exits from the discharge space. The complexity of the electrical and/or electronic system is advantageously reduced. The overall complexity of the system is reduced.

According to an embodiment, the system comprises at least one ground electrode. The at least one high voltage electrode and the at least one ground electrode may be formed for generating an electromagnetic field for generating a plasma in the discharge space.

This ensures in particular that the plasma generation is independent of a distance of a surface to be treated, which then otherwise acts as a counter-electrode and significantly influences the properties of the plasma.

In an embodiment, the system has at least one high voltage electrode and at least one ground electrode for generating an electromagnetic field for generating a plasma in the discharge space.

The plasma exiting through the second opening is controlled by a flow controller of the system, which is formed to set a volume flow of the working gas through the first opening from a working gas source into the discharge space. The flow controller is further formed to adopt at least a first state and a second state. In the first state, no working gas is supplied from the working gas source to the discharge space, so that even with generated, in particular generated by the ground electrode and the high voltage electrode, electromagnetic field in the discharge space no plasma exits from the second opening. In other words, this means that in the first state, no working gas is supplied from the working gas source to the discharge space, so that even with existing electromagnetic field in the discharge space, no plasma exits from the second opening. In the second state, the working gas from the working gas source is supplied to the discharge space. In the discharge space plasma is generated and the plasma exits from the second opening.

An electromagnetic field is generatable between the high voltage electrode and the ground electrode when voltage is applied. The generated electromagnetic field is also referred to as the existing electromagnetic field in this application. With the aid of the generated or existing electromagnetic field, a non-thermal atmospheric pressure plasma is generatable.

In an embodiment, a ground electrode is arranged at the discharge space.

An advantage of an embodiment having a ground electrode is that the electromagnetic field is generated and/or set more precisely. This also allows characteristics of the generated plasma to be set more precisely.

In an embodiment, the system is configured to generate a modulation of the plasma by a corresponding modulation of the volume flow of the working gas, in particular exclusively by a corresponding modulation of the volume flow of the working gas and in particular not by a modulation of the electromagnetic field, in particular wherein the system is configured to generate only a continuous electromagnetic field in the discharge space. In an embodiment, the system is formed, particularly during the modulation of the plasma, to generate only a continuous electromagnetic field in the discharge space.

Modulation of the plasma means in particular a variation of the plasma jet. Modulation of the plasma may mean that the plasma is converted from a status, in which it exits the discharge space, in particular as a plasma jet, to another status, in which it does not exit the discharge space, i.e. no more plasma jet exits the discharge space. The modulation of the plasma may be such that a distance by which the plasma jet exits the discharge space through the second opening is varied. The distance may be shortened, particularly to a minimum distance. If the distance falls below the minimum distance, no plasma exits the discharge space. Alternatively, it is provided that the distance can be increased.

One embodiment is characterized in that the modulation of the plasma is generated by a corresponding modulation of the working gas volume flow. If no working gas volume flow is generated, no plasma jet exits the discharge space. In the case a volume flow of the working gas is present, a plasma jet can exit through the second opening of the discharge space.

The working gas volume flow can be pulsed. A pulsed working gas volume flow is a non-continuous volume flow that varies in amount over time.

The plasma can be modulated by modulation of the working gas volume flow. Furthermore, the consumption of the working gas can be controlled. In an embodiment, the consumption of the working gas is regulated. In an embodiment according to the invention, a duration and/or an effect of a leakage current is controlled. A leakage current may occur when the plasma (the plasma jet) contacts a surface. If no plasma jet exits the discharge space, there is no leakage current to a surface.

A continuous electromagnetic field is understood to be in particular an electromagnetic field which is continuously switched on and continues to exist even when no working gas volume flow is passing through the discharge space. In this sense, the term "continuous" is also to be regarded as permanent or constant (apart from the implicit time dependence of an electromagnetic field due to the alternation of the electric and magnetic portions of the field).

In an embodiment, the electromagnetic field is a continuous electromagnetic field. In particular, the electromagnetic field is continuous with respect to the amplitude of the field strength. In an embodiment, the electromagnetic field is time-averaged constant.

An embodiment is characterized in that the continuous electromagnetic field is generated with the aid of a DC voltage. According to the invention, in order to achieve a modulation of the plasma, the applied DC voltage is not modulated.

In an alternative embodiment, the electromagnetic field is generated using an AC voltage. To modulate the plasma, the applied AC voltage is not modulated.

The electromagnetic field is used only to generate the plasma. According to the invention, the electromagnetic field is not used to modulate the plasma. In particular, the electromagnetic field is not modulated to modulate the plasma. In particular, the electromagnetic field is not modulated to generate an exit of the plasma (plasma jet) from the discharge space and/or to terminate an exit of the plasma from the discharge space. The exit of the plasma jet from the discharge space can be controlled by the working gas volume flow.

According to a further embodiment, the flow controller is formed to modulate the volume flow of the working gas.

In an embodiment, the working gas volume flow is settable with the aid of the flow controller.

The flow controller may be formed as a discrete directional control valve. A discrete directional control valve can switch discretely between a first state (closed) and a second state (open).

In an alternative embodiment, the flow controller is a proportional valve. A proportional valve can achieve continuous transitions of a valve opening. I.e., the proportional valve imparts partial opening and/or closing so that a passage of the working gas can be precisely dosed.

Modulation of the working gas volume flow can take place by controlling the flow controller. For example, transitioning the flow controller from its first state to its second state can result in a working gas volume flow in the discharge space that allows the plasma to exit the discharge space as a plasma jet. An alternative modulation may result from converting the flow controller from its second state to its first state. Transitioning the flow controller from its second state to its first state may terminate a working gas volume flow in the discharge space, such that the plasma no longer exits the discharge space.

This means that the flow controller can be used to control the working gas volume flow. The working gas volume flow can be used to control the exit of the plasma from the discharge space. The flow controller can provide fluid dynamic control of the plasma. In particular, the plasma is modulatable without controlling the electromagnetic field. Plasma exit from the discharge space is therefore possible in a simple manner without changing the applied electromagnetic field.

By precisely dosing the working gas, the distance by which the plasma jet exits the discharge space can be precisely set and/or varied.

In an embodiment, the flow controller is controlled electronically. In an embodiment, the flow controller is electrically controlled. This means that fluid dynamic control of the plasma is provided by means of electrical or electronic control of the flow controller.

One embodiment is characterized in that the flow controller has a short switching time. A short switching time means that the flow controller can switch quickly between the individual states.

In an embodiment, the system is formed to transition the flow controller from the first state to the second state such that when an electromagnetic field is generated in the discharge space, plasma is generated in the discharge space and exits the discharge space through the second opening. In an embodiment, the system is formed to transition the flow controller from the second state to the first state such that with a generated electromagnetic field in the discharge space, no plasma does exits the discharge space. In an embodiment, the system is configured to transition the flow controller from the first state to the second state as well as to transition the flow controller from the second state to the first state.

In other words, the flow controller is formed to switch on the plasma jet, i.e. plasma exits the discharge space as a plasma jet after no plasma has exited the discharge space before. In an embodiment, the system is configured to switch off the plasma jet. This means that no plasma jet exits the discharge space after a plasma jet has previously exited the discharge space.

One embodiment is characterized in that the flow controller has an active actuator formed to adopt at least the first or the second state.

The active actuator is, for example, a valve, particularly a magnetic valve. The active actuator can be controlled electrically.

An active actuator may be formed as a discrete directional valve that adopts the first or second state. In an embodiment, the active actuator is formed as a proportional valve.

The active actuator can be a piezo valve. With the aid of a piezo valve, the flow of the working gas can be dosed quickly and precisely. A piezo valve consumes very little energy. This is particularly advantageous when the system is used as a hand-held device, as a battery lasts longer in this case and fewer battery changes or charging cycles are required. This increases the convenience as well as the possible applications of the system, in particular the possibility of mobile use of the system.

In an embodiment, the working gas source delivers working gas constantly (uniformly over time). With the aid of the active actuator, a working gas volume flow pulsed over time is introducable into the discharge space.

In an embodiment, the flow controller comprises a passive actuator formed to adopt at least one of the first and second states, wherein the passive actuator can be transitioned from the first state to the second state particularly by the volume flow of the working gas.

The passive actuator can be a flutter valve or a check valve.

The active and/or passive actuator can be a microvalve. A micro valve advantageously allows space-saving installation of the flow controller. This means that the space required for the system can be kept small. This is particularly advantageous when the system is used as a hand-held device.

According to a further embodiment, the system has a working gas source having the flow controller.

The working gas source can, for example, have a control element with the aid of which it can be used to set whether working gas flows out of the working source. In an embodiment, the outflow of the working gas, and thus the working gas volume flow, is dosed with the aid of a control element. In an embodiment, the system is arranged for a pulsed working gas volume flow to exit the working gas source and flow into the discharge space.

In an embodiment, the system has an automatic control unit formed to control the flow controller. With the aid of the automatic control unit, the flow controller can be automatically set to the first state or to the second state. Furthermore, in an embodiment, the automatic control unit is formed to transition the flow controller to the second state for a selected time period, so that a time period can be set over which the working gas is introduced into the discharge space.

With the aid of the automatic control unit, it can be controlled whether working gas can flow into the discharge space. In an embodiment, the automatic control unit controls the working gas volume flow.

In an embodiment, the automatic control unit comprises a microcontroller and a high-voltage coil.

The automatic control unit can control that the flow controller is in the second state for a selected time period. This means that the automatic control unit can control that there is a working gas volume flow in the discharge space for the selected time period.

In an embodiment, the automatic control unit controls a switch-on of the plasma jet. The automatic control unit can control over what time period the plasma jet is switched on. Further, in an embodiment, the automatic control unit controls the distance by which the plasma jet exits the discharge space through the second opening. In an embodiment, the automatic control unit controls a switch-off of the plasma jet. The automatic control unit may be arranged to switch off the plasma jet for a time period after the plasma jet has previously been switched on for another time period. In an embodiment, the automatic control unit is configured to switch on the plasma jet for a selected time period after the plasma jet was previously switched off for another selected time period.

One embodiment of the automatic control unit is formed to precisely dose the working gas flowing into the discharge space, for example by controlling a proportional valve.

The automatic control unit can be programmable.

An advantage of the embodiment is that it is automatically controlled when and for how long (i.e., over what time period) a plasma jet exits the discharge space. Thus, for example, a treatment duration can be automatically controlled by means of the plasma jet.

In an embodiment, the automatic control unit is configured to regulate the working gas volume flow. In an embodiment, the system has a feedback mechanism for regulation.

Advantageously, the feedback mechanism automatically detects and counteracts any fluctuation (deviation from a control value) of the plasma, for example by modulating the working gas volume flow. The fluctuation is compensated so that a uniform plasma jet exits over time.

In accordance with an embodiment, the system comprises a mixing arrangement, formed to mix a further gas with the working gas so that the resulting gas mixture is introducable into the discharge space. In particular, the system is configured such that the flow controller has the mixing arrangement.

In an embodiment, the mixing arrangement is configured to mix a plurality of gases with the working gas. One embodiment provides for a gas mixture to be mixed with the working gas, in particular to be mixed in the mixing arrangement.

The further gas is in particular one of the following gases: Hydrogen, oxygen, nitrogen, water vapor, argon, helium, neon, krypton, or carbon dioxide. The admixed gas mixture comprises in particular one of the following gases: Hydrogen, oxygen, nitrogen, water vapor, argon, helium, neon, krypton, or carbon dioxide. The admixed gas mixture may be air, particularly ambient air. In an embodiment, the admixed gas mixture is a humidified gas. In particular, the admixed gas mixture may comprise water vapor, as well as at least one of the following gases: Hydrogen, oxygen, nitrogen, water vapor, argon, helium, neon, krypton, or carbon dioxide.

Thus, a gas mixture different from the working gas is introducable into the discharge space and other reactive species is generatable there.

In an embodiment, the system is arranged to admix the further gas with the working gas for a selected duration. Thus, the composition of the gas or gas mixture introduced into the discharge space can be set in a time-resolved manner. In an embodiment, time-resolved control of the composition of the gas or gas mixture introduced into the discharge space is possible.

In an embodiment, the system is formed to generate a capacitively-coupled plasma. One embodiment is characterized in that the system is formed to generate an inductively-coupled plasma. In an embodiment, the system is formed to generate a microwave-induced plasma. In an alternative embodiment, the system is formed to generate a plasma using dielectrically hindered discharge.

In a further embodiment, the system has a plurality of discharge spaces, wherein each discharge space comprises a respective first opening through which a working gas is introducable into the respective discharge space, wherein each discharge space comprises an assigned second opening through which the plasma can exit the respective discharge space. At least one high-voltage electrode for generating an electromagnetic field for generating a plasma in the respective discharge space is assigned to each discharge space, so that a plasma is generatable in each discharge space independently of the other discharge spaces. The plasma exiting through the assigned second opening is controlled by a flow controller of the system with the respective discharge space, wherein each flow controller is formed to set a volume flow of the working gas through the respective first opening of the respective discharge space from a working gas source into the respective discharge space. Further, the respective flow controller is formed to adopt at least a first state and a second state. In the first state, no working gas is supplied from the working gas source to the respective discharge space, so that even with generated plasma in the respective discharge space, no plasma exits the assigned second opening in the respective discharge space. In the second state, the working gas from the working gas source is supplied to the respective discharge space of the plurality of discharge spaces and a plasma is generated therein, and the plasma exits the respective second opening.

In a further embodiment, the system has a plurality of discharge spaces, wherein each discharge space of the plurality of discharge spaces has a respective first opening through which a working gas is introducable into the respective discharge space of the plurality of discharge spaces. Each discharge space of the plurality of discharge spaces has an assigned second opening through which plasma can exit the respective discharge space of the plurality of discharge spaces. Further, each discharge space of the plurality of discharge spaces has assigned thereto at least one high voltage electrode for generating an electromagnetic field for generating a plasma in the respective discharge space of the plurality of discharge spaces. A plasma is generatable in each discharge space of the plurality of discharge spaces independently of the other discharge spaces of the plurality of discharge spaces, wherein the plasma exiting through the assigned second opening is controlled by a flow controller of a plurality of flow controllers of the system assigned with the respective discharge space of the plurality of discharge spaces. Each flow controller of the plurality of flow controllers is formed to set a volume flow of the working gas through the respective first opening of the respective discharge space of the plurality of discharge spaces from a working gas source into the respective discharge space of the plurality of discharge spaces, wherein the respective flow controller of the plurality of flow controllers is further formed to adopt at least a first state and a second state. In the first state, no working gas is supplied from the working gas source to the respective discharge space of the plurality of discharge spaces, such that in the respective discharge space of the plurality of discharge spaces even with generated electromagnetic field in the respective discharge space of the plurality of discharge spaces no plasma exits the assigned second opening. In the second state, the working gas from the working gas source is supplied to the respective discharge space of the plurality of discharge spaces to generate a plasma therein, and the plasma exits the second opening, respectively.

Each discharge space (of the plurality of discharge spaces) is assigned at least one high-voltage electrode for generating an electromagnetic field for generating a plasma in the respective discharge space (of the plurality of discharge spaces), in particular wherein at least one high-voltage electrode for generating an electromagnetic field for generating a plasma in the respective discharge space (of the plurality of discharge spaces) is arranged in each discharge space (of the plurality of discharge spaces), so that a plasma is generatable in each discharge space (of the plurality of discharge spaces) independently of the other discharge spaces (of the plurality of discharge spaces).

In particular, the high-voltage electrodes can be short-circuited to each other.

In one embodiment, the discharge spaces of the plurality of discharge spaces are identically formed. In an alternative embodiment, at least one discharge space of the plurality of discharge spaces is different from the other discharge spaces.

One advantage about a system with a plurality of discharge spaces is that a larger area, such as a surface of an object, can be treated with plasma without having to move the system and/or the object to be treated.

Such a system can be used for large-area surface treatment, particularly for thermally sensitive surface treatment.

Each flow controller of the plurality of flow controllers can be controlled electrically or electronically. The control of an assigned flow controller controls the working gas volume flow in the respective discharge space and thus the plasma, in particular whether plasma in the form of a plasma jet exits the respective discharge space or not. This means that fluid-dynamic control of the plasma, in particular of the plasma jet, takes place through the electrical or electronic control of the respective flow controller.

This reduces the technical complexity of controlling the plasma in a system that has a plurality of discharge spaces. Flawless operation of the system is made possible in a simple manner.

One embodiment is characterized in that at least one ground electrode is assigned to each discharge space. In an embodiment, the at least one high-voltage electrode and the at least one ground electrode are arranged for generating an electromagnetic field for generating a plasma in the respective discharge space. The system is thereby particularly configured to ignite the plasma, in particular in the volume flow of the working gas, immediately by the electromagnetic field of the high-voltage electrode.

In one embodiment, the system has a plurality of discharge spaces, wherein each discharge space of the plurality of discharge spaces has a respective first opening through which a working gas is introducable into the respective discharge space of the plurality of discharge spaces. Each discharge space of the plurality of discharge spaces has an assigned second opening through which plasma can exit the respective discharge space of the plurality of discharge spaces. Further, each discharge space of the plurality of discharge spaces has assigned thereto at least one high voltage electrode and at least one ground electrode for generating an electromagnetic field for generating a plasma in the respective discharge space of the plurality of discharge spaces. In each discharge space of the plurality of discharge spaces, a plasma is generatable independently of the other discharge spaces of the plurality of discharge spaces, wherein the plasma exiting through the assigned second opening is controlled by a flow controller of a plurality of flow controllers of the system assigned to the respective discharge space of the plurality of discharge spaces. Each flow controller of the plurality of flow controllers is formed to set a volume flow of the working gas through the respective first opening of the respective discharge space of the plurality of discharge spaces from a working gas source into the respective discharge space of the plurality of discharge spaces, wherein the respective flow controller of the plurality of flow controllers is further formed to adopt at least a first state and a second state. In the first state, no working gas is supplied from the working gas source to the respective discharge space of the plurality of discharge spaces, such that no plasma exits the assigned second opening in the respective discharge space of the plurality of discharge spaces even with generated electromagnetic field in the respective discharge space of the plurality of discharge spaces. In the second state, the working gas from the working gas source is supplied to the respective discharge space of the plurality of discharge spaces to generate a plasma therein, and the plasma exits from the respective second opening.

Each discharge space (of the plurality of discharge spaces) is assigned at least one high-voltage electrode and at least one ground electrode for generating an electromagnetic field for generating a plasma in the respective discharge space (of the plurality of discharge spaces), in particular wherein at least one high-voltage electrode and at least one ground electrode for generating an electromagnetic field for generating a plasma in the respective discharge space (of the plurality of discharge spaces) are arranged at each discharge space (of the plurality of discharge spaces), so that a plasma is generatable in each discharge space (of the plurality of discharge spaces) independently of the other discharge spaces (of the plurality of discharge spaces).

In an embodiment, the system has an automatic control system. The automatic control system is formed to independently control the plurality of flow controllers of the system such that the flow controllers can independently adopt at least the first state or the second state such that plasma is generated only in a selected discharge space and exits only from the second opening of the selected discharge space.

The automatic control system can control each flow controller of the plurality of flow controllers individually. This means that each flow controller of the plurality of flow controllers can be controlled independently of the other flow controllers.

In an embodiment, the automatic control system is formed to control each flow controller of the plurality of flow controllers individually, so that each flow controller of the plurality of flow controllers is controllable independently of the remaining flow controllers.

In an embodiment, the automatic control system is arranged such that each flow controller of the plurality of flow controllers is controlled such that the plasma jet of the respective assigned discharge space exhibits a selected temporal pattern, i.e., a selected sequence of phases in which a plasma jet exits the respective assigned discharge space and other phases in which a plasma jet does not exit.

According to an embodiment, the automatic control system is formed to control the flow controllers of the plurality of flow controllers of the system independently of each other, so that a selected flow controller of the plurality of flow controllers adopts the second state for a first time period and all other flow controllers of the plurality of flow controllers adopt the first state, and after the first time period, the selected flow controller of the plurality of flow controllers adopts the first state and another selected flow controller of the plurality of flow controllers adopts the second state for a second time period, wherein the first and second time periods are consecutive or temporarily overlap.

The automatic control system can control from which selected discharge space a plasma jet exits. In particular, the automatic control system is formed to ensure that a plasma jet exits at any timepoint from a selected discharge space of the plurality of discharge spaces.

In an embodiment, the automatic control system is configured to control the flow controllers of the plurality of flow controllers such that the first time period and the second time period follow each other without interruption. In other words, in an embodiment, the automatic control system is configured to control the flow controllers of the plurality of flow controllers such that a plasma jet exits from exactly one discharge space of the plurality of discharge spaces at any timepoint.

In an alternative embodiment, the automatic control system is configured to control the flow controllers of the plurality of flow controllers such that the first time period and the second time period temporarily overlap, wherein in particular the first time period and the second time period are not completely overlapped. This means that in an embodiment, the system is configured such that in the overlapping time period of the first time period and the second time period, one plasma jet exits from each of the two discharge spaces (to which the flow controller and the other flow controller are assigned), respectively. One embodiment provides that the overlap period is short, in particular shorter than 1 s.

In an embodiment, the system is formed to allow each discharge space of the plurality of discharge spaces to be connectable or connected to a common working gas source.

In each discharge space, the same reactive species are generatable.

This embodiment is particularly advantageous when the system is used for large-area treatment with a plasma, wherein the same species are to act over the entire area.

According to a further embodiment, at least one flow controller of the plurality of flow controllers has a mixing arrangement with which a further gas is mixed with the working gas so that a resulting gas mixture is introducable into the respective discharge space of the plurality of discharge spaces. This means that a further gas can be mixed with the working gas in a spatially resolved manner, for example in a discharge space arranged at a selected position relative to the other discharge spaces of the system. Thus, in a spatially resolved manner, e.g. in a selected local region, the effectiveness of the plasma can be adapted to specific requirements, for example in the treatment of large wound areas.

In a further embodiment, the system is formed to have at least one discharge space of the plurality of discharge spaces connectable or connected to a dedicated working gas source.

A reactive species can be formed in the at least one discharge space that is differing from a reactive species that can be formed in the other discharge spaces.

This embodiment is particularly advantageous when the system is used for large-area treatment with a plasma, wherein the area has at least one sub-area on which at least one species is to act, which is differing from a reactive species arising in the other discharge spaces. In other words, this means that for the treatment of the at least one sub-area, the effectiveness of the plasma can be adapted to meet requirements.

One embodiment is characterized in that the second openings of the plurality of discharge spaces face in the same direction.

In particular, the surface normals of the second openings point in the same direction.

An advantage of such an arrangement is that plasma jets can be directed onto a surface with such a system.

According to a further embodiment, the second openings of the plurality of discharge spaces are positioned or positionable to face a central region.

In particular, the surface normals of the second openings face a central region.

In an embodiment, the second openings of the plurality of discharge spaces are oriented toward a common volume.

With such a system, plasma jets can be directed at the surface of an object from a variety of directions.

In an embodiment, the second openings of the plurality of discharge spaces are arranged in a common plane.

In an embodiment, the second openings of the plurality of discharge spaces are arranged in a common plane, wherein the second openings of the plurality of discharge spaces cover an area of at least 10 cm$^2$, particularly at least 50 cm$^2$, particularly at least 100 cm$^2$.

According to a further embodiment, the system has at least 2 discharge spaces, in particular at least 5 discharge spaces, in particular at least 10 discharge spaces, in particular at least 20 discharge spaces.

According to a further embodiment of the invention, the at least one flow controller is continuously controllable so that the volume flow through each discharge space is continuously and individually settable.

According to a further embodiment of the invention, the at least one flow controller is a proportional valve.

According to a further embodiment of the invention, the system is configured to modulate the volume flow of the working gas in each discharge space by means of the flow controller, wherein the modulation of the volume flow has more than two modulation states, in particular wherein the modulation of the volumetric flow is continuously settable.

According to a further embodiment of the invention, each flow controller is configured to have a control time between 0.1 ms and 1 s, so that the volume flow can be modulated with a respective time resolution.

According to a further embodiment of the invention, the system comprises at least one associated sensor for each discharge space, which sensor detects a plasma parameter and is configured to output a sensor signal indicative of the plasma parameter, wherein the system is configured to control the at least one flow controller on the basis of the sensor signal in such a way that a plasma parameter to be achieved is set for the respectively assigned discharge space.

According to a further embodiment of the invention, the system comprises exactly one high-voltage electrode and no more than two ground electrodes per discharge space.

According to a further embodiment of the invention, the system is configured to generate a capacitively-coupled plasma, an inductively-coupled plasma, and/or a microwave-induced plasma in the volume flow of the working gas supplied through the first opening.

According to a further embodiment of the invention, each discharge space has exactly two openings—the first opening and the second opening.

Another aspect of the invention relates to a method for generating and controlling a non-thermal atmospheric pressure plasma utilizing a system according to the invention. Thereby, the method comprises the following steps:

Generating an electromagnetic field in the discharge space,

Setting the flow controller to a first state or a second state, wherein in the first state no working gas is supplied from the working gas source to the discharge space, so that even with generated electromagnetic field in the discharge space no plasma exits the discharge space, and wherein in the second state the working gas is supplied from the working gas source to the discharge space, a plasma is generated in the discharge space, and the plasma exits from the second opening.

In an embodiment, the plasma is regulated.

One embodiment of the method has the following steps:

Generating an electromagnetic field in each discharge space of the plurality of discharge spaces, Setting each flow controller of the plurality of flow controller to a first state or a second state, wherein in the first state no working gas from the working gas source is supplied to the respective discharge space of the plurality of discharge spaces, so that in the respective discharge space of the plurality of discharge spaces, even with generated electromagnetic field in the respective discharge space of the plurality of discharge spaces, no plasma exits from the respective discharge space, and wherein, in the second state, the working gas from the working gas source is supplied to the respective discharge space of the plurality of discharge spaces, a plasma is generated in the respective discharge space of the plurality of discharge spaces, and the plasma exits from the assigned second opening.

In an embodiment, the method is characterized in that the volume flow of the working gas supplied to the discharge space or a selected discharge space of the plurality of discharge spaces is modulated to generate a modulation of the plasma while a continuous electromagnetic field is generated in the discharge space or the selected discharge space of the plurality of discharge spaces.

According to an embodiment, a flow controller of the plurality of flow controllers is controlled to adopt the second state for a first time period and all other flow controllers of the plurality of flow controllers are controlled to adopt the first state, and after the first time period, the flow controller of the plurality of flow controllers is converted to the first state and another flow controller of the plurality of flow controllers is converted to the second state consecutive to or overlapping the first time period and adopts the second state for a second time period, while the remaining other flow controllers of the plurality of flow controllers remain in the first state.

This means that a plasma jet exits from a selected discharge space of the plurality of discharge spaces, while no plasma jet exits from the other discharge spaces.

The plurality of flow controllers can be controlled as such that different selected flow controllers consecutively convert from the respective first state to the respective second state. This means that plasma jets can exit successively from different selected discharge spaces, wherein a plasma jet exits particularly from only one selected discharge space of the plurality of discharge spaces at a time.

In accordance with an embodiment, the automatic control system controls the plurality of flow controllers such that each flow controller of the plurality of flow controllers switches between the first state and the second state and/or between the second state and the first state in a selected order independently of the other flow controllers of the plurality of flow controllers.

Each flow controller of the plurality of flow controllers can be controlled independently of the other flow controllers. In particular, each flow controller of the plurality can be controlled independently of the other flow controllers such that a plasma jet exits the respective discharge space (second state) or no plasma jet exits (first state). The automatic control system can thereby control the plurality of flow controllers such that a plasma jet exits only a selected discharge space of the plurality of discharge spaces at any given time.

By means of a system according to the invention, a plasma jet can be controlled in a simple manner. An embodiment of the system is configured for a plurality of plasma beams to be controlled and/or regulated in a coordinated manner. The electrical and/or electronic complexity of the system is advantageously reduced compared to a prior art system. The overall complexity of the system according to the invention is reduced. This reduces the production costs of such a system and is thus economically advantageous.

In the following, embodiments as well as features and advantages of the invention are explained with reference to the figures. Showing:

FIG. 1 a schematic representation of an embodiment of a system according to the invention with a discharge space in which the flow controller adopts the first state, FIG. 2 the system of FIG. 1, in which the flow controller adopts the second state, FIG. 3 a schematic representation of a system according to the invention with flow controller in the second state, FIG. 4 a schematic representation of a system in which the flow controller adopts the first state, FIG. 5 a schematic representation of an embodiment of a system according to the invention, with the flow controller in the first state, FIG. 6 a schematic representation of a system according to the invention, in which the flow controller adopts the first state, FIG. 7a)-7f) different views of a handheld device of a system with a plurality of discharge spaces, FIG. 8 a schematic representation of an embodiment of a system according to the invention with three discharge spaces whose assigned flow controllers adopt the first state, FIG. 9 a schematic representation of the system of FIG. 8, wherein a flow controller adopts the second state, FIG. 10 a schematic representation of a system according to the invention with two discharge spaces, wherein a flow controller adopts the first state and one flow controller adopts the second state, wherein the system has a working gas source, FIG. 11 a schematic diagram of a system having two discharge spaces, wherein a flow controller adopts the first state and a flow controller adopts the second state, wherein the system has two working gas sources, FIG. 12 a schematic representation of a system according to the invention with a mixing arrangement and two discharge spaces, wherein a flow controller adopts the first state and a flow controller adopts the second state, FIG. 13 a frontal view of a system having a plurality of discharge spaces with second openings facing a central region, FIG. 14 a cross-section of the system of FIG. 13, and FIG. 15 a frontal view of a system having a plurality of discharge spaces with second openings facing a central region.

Figure 1:
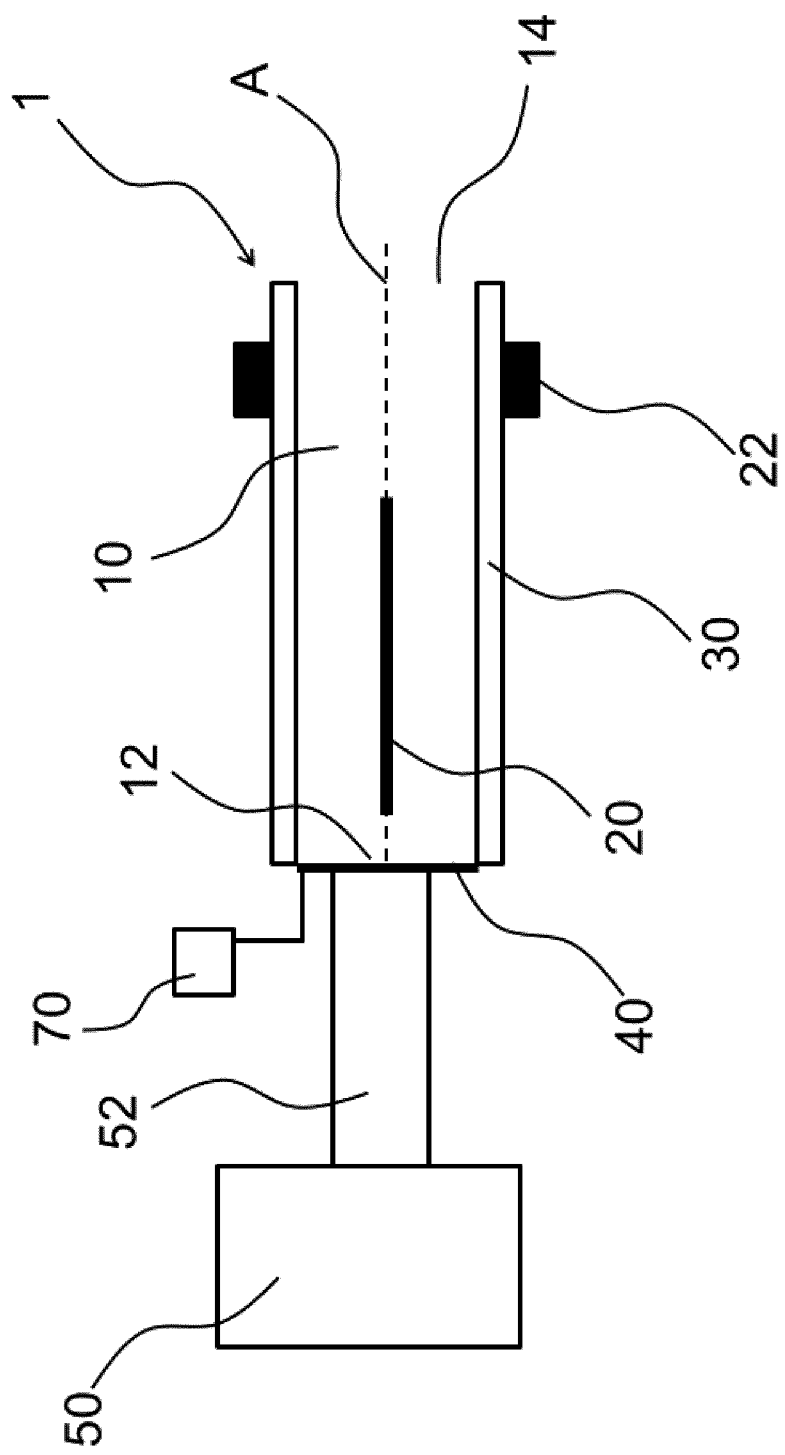
FIGS. 1 and 2 shows a system 1 for generating and controlling a non-thermal atmospheric pressure plasma (plasma) having a discharge space 10 and a flow controller 40, wherein the flow controller 40 is in a first state (FIG. 1) and a second state (FIG. 2), respectively.
Figure 2:
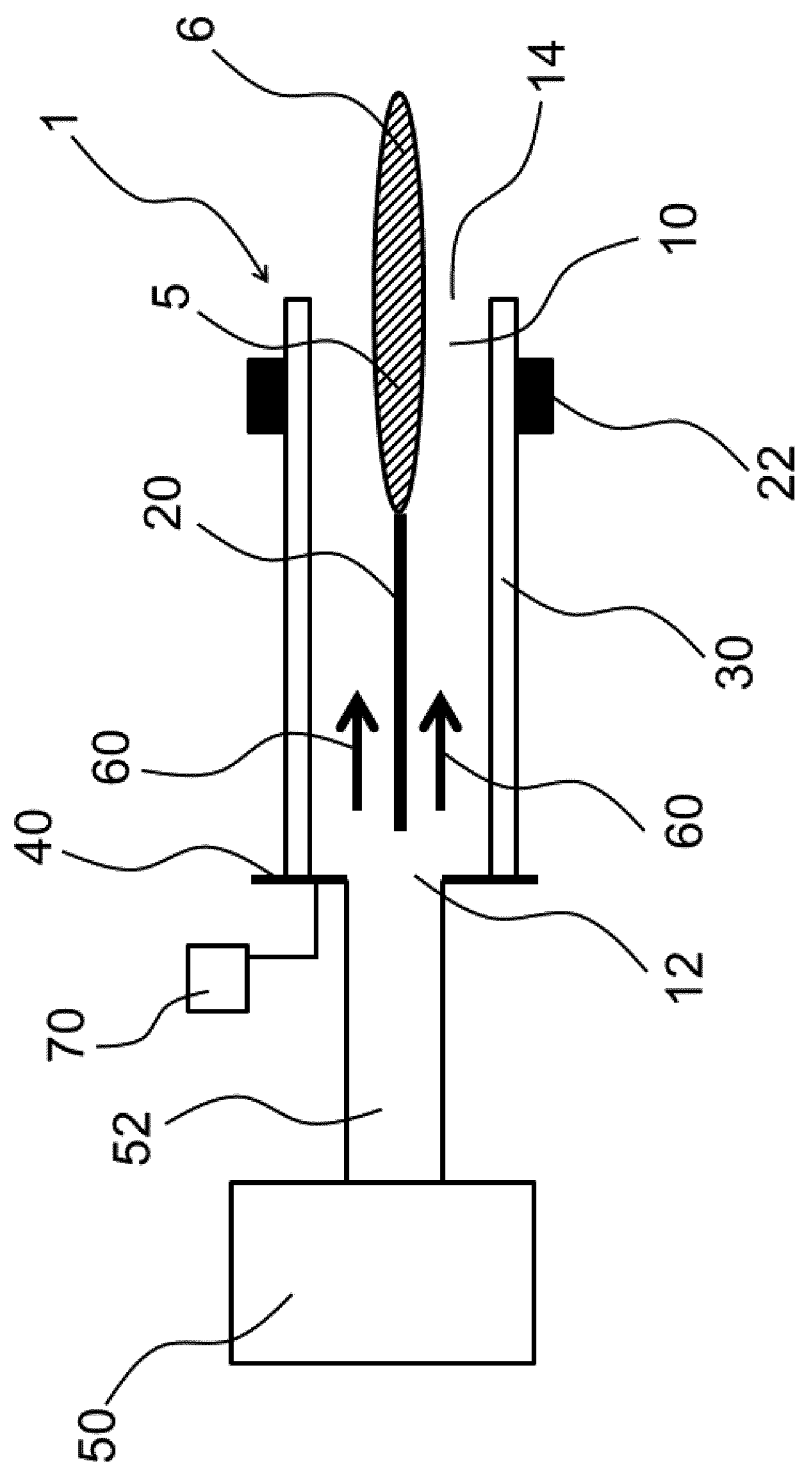
Figure 3:
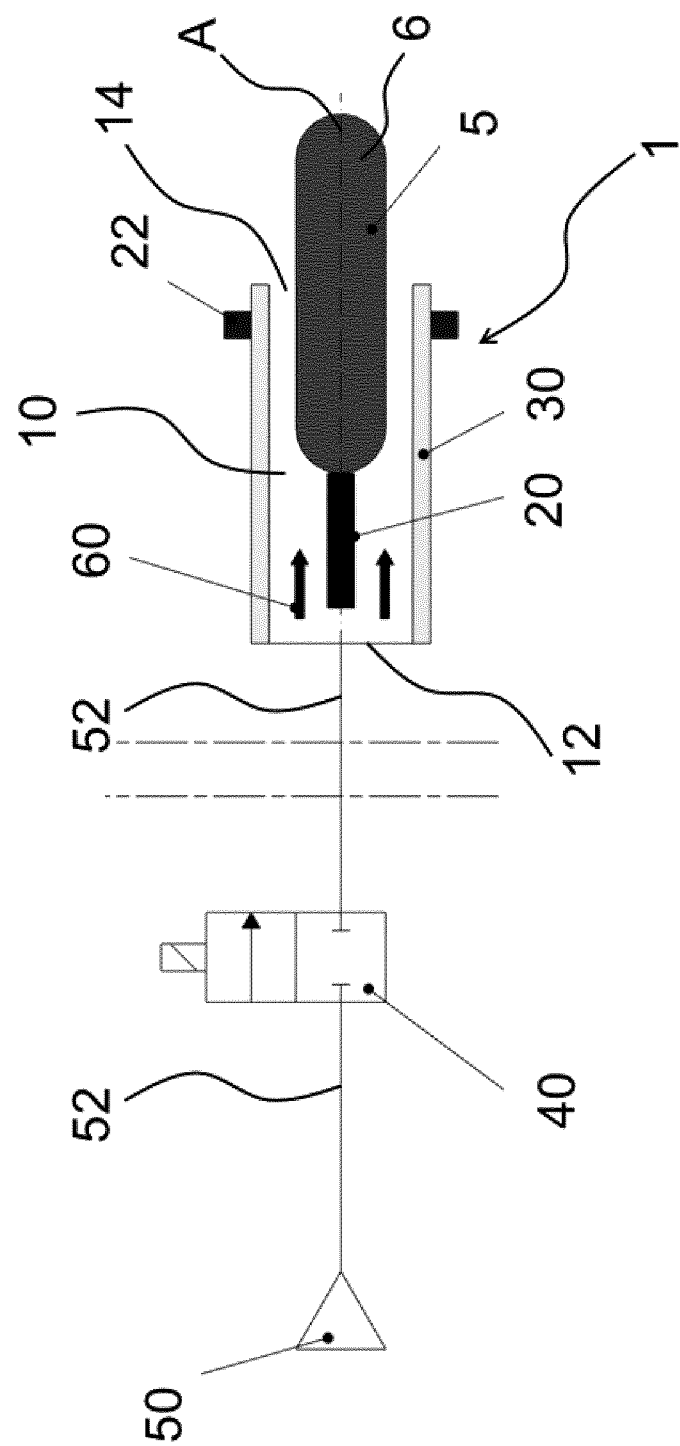
In FIG. 3, a further embodiment is illustrated, wherein the state is shown in which the flow controller 40 is in the second state.

The discharge space 10 has a first opening 12 and a second opening 14. In an embodiment according to the invention, the discharge space 10 is delimited by a dielectric 30 (FIG. 1, FIG. 2, FIG. 3). The dielectric 30 may be formed in the form of a cylindrical shell.

The discharge space 10 extends along a longitudinal axis A. In the embodiment shown, the first opening 12 is located opposite the second opening 14.

The system 1 shown has a high voltage electrode 20 arranged within the discharge space 10 (FIG. 1-FIG. 4). A ground electrode 22 is arranged outside the discharge space 10 at the dielectric 30, wherein the ground electrode 22 is arranged near the second opening 14 (FIG. 1-FIG. 4). With the aid of the high-voltage electrode 20 and the ground electrode 22, an electromagnetic field is generated in the discharge space 10 when voltage is applied (FIG. 1-FIG. 4).

Figure 5:
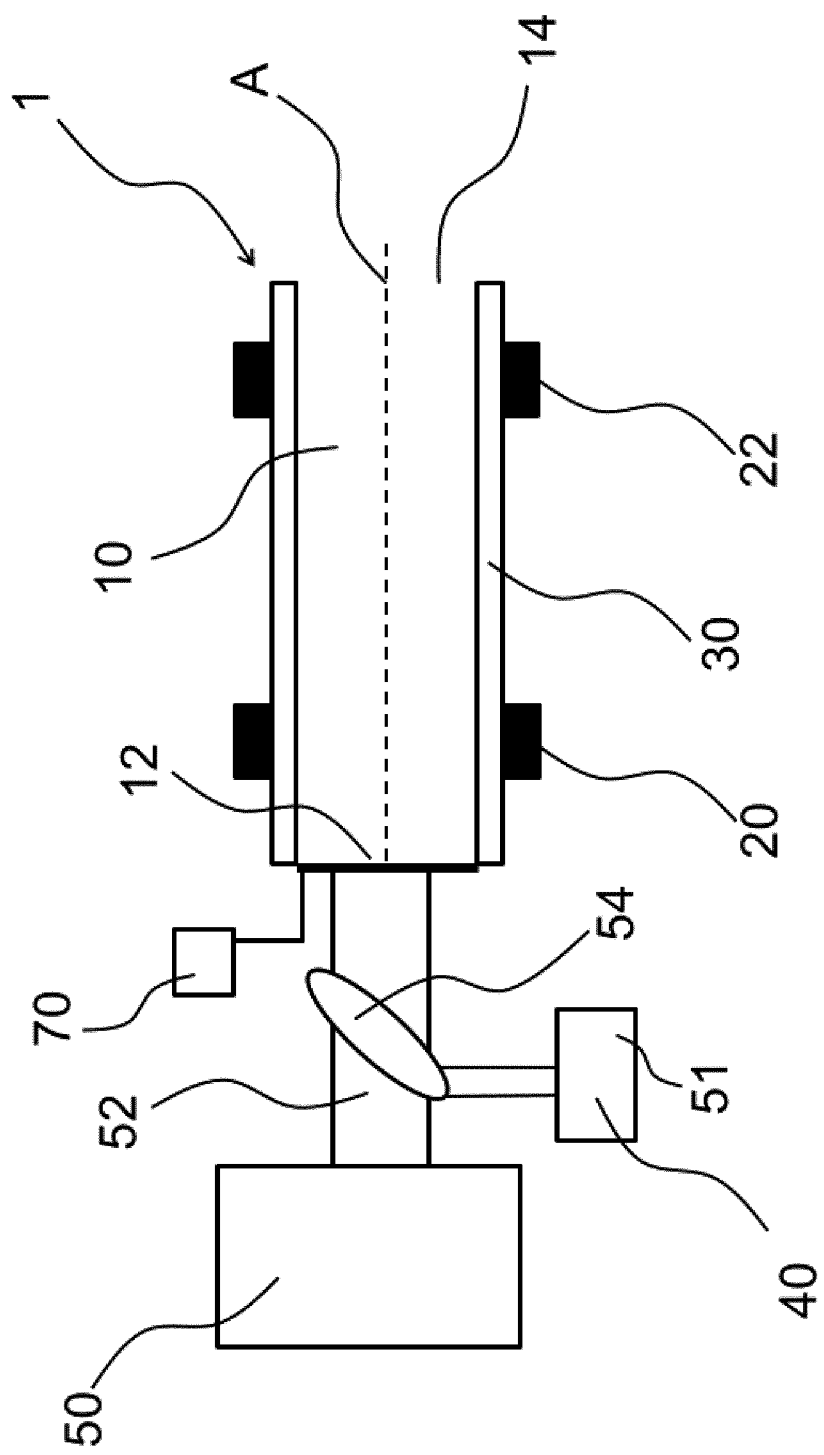

In an embodiment, the high voltage electrode 20 and the ground electrode 22 are arranged outside the discharge space 10 at the dielectric 30 (FIG. 5).

Figure 6:
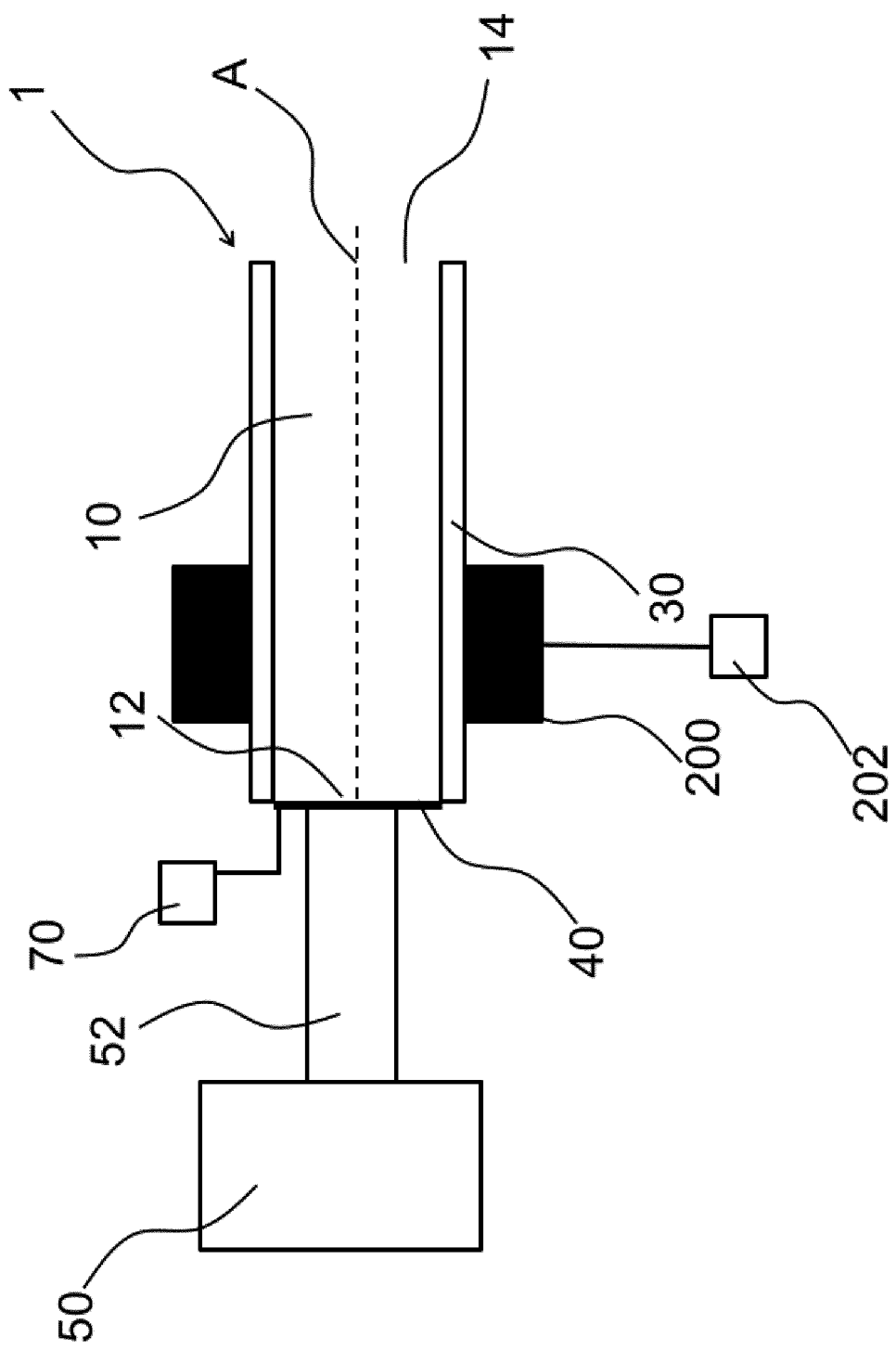

The system 1 may have a microwave generator 202 and a microwave resonator 200 (FIG. 6).

Figure 4:
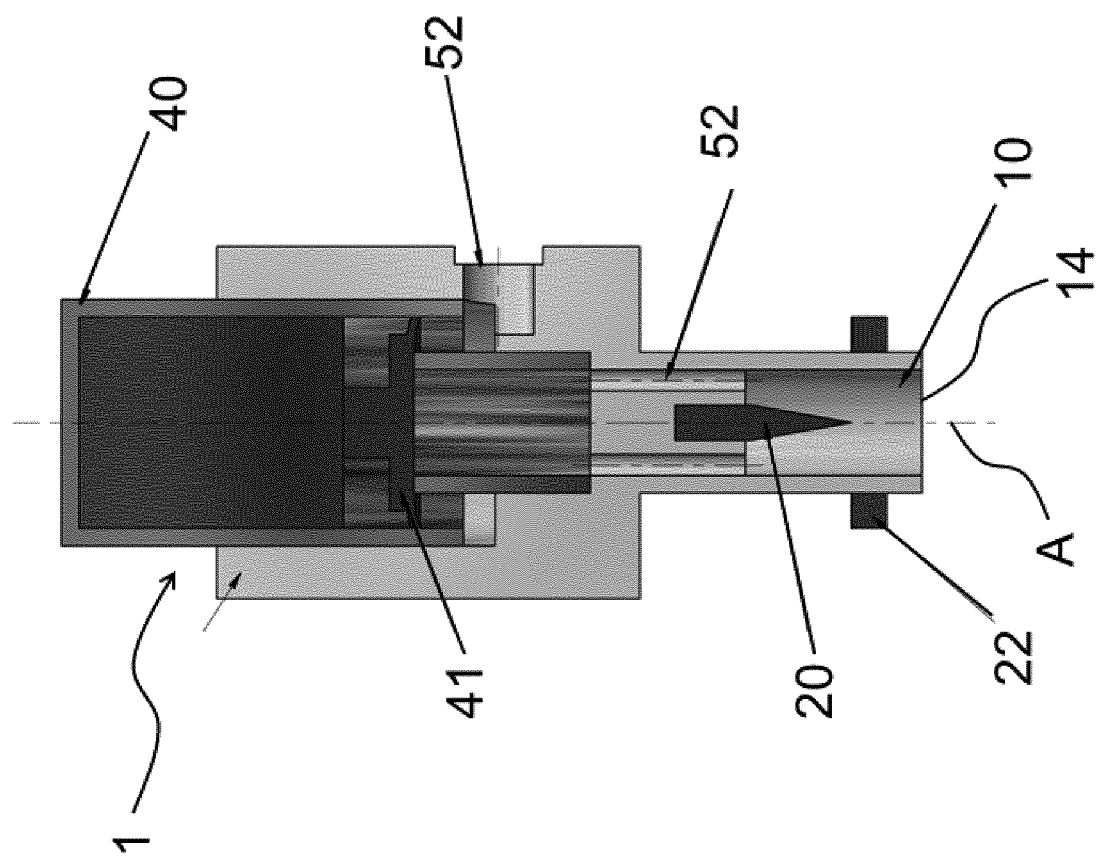
FIGS. 4-6 show further embodiments in which the respective flow controllers adopt the first state, such that no plasma jet exits.

The discharge space 10 may be connected to a working gas source 50 by means of a conduit element 52, in particular by means of a gas conduit element. The conduit element 52 can on the one hand be fluidically connected to the discharge space 10 and on the other hand to the working gas source 50 (FIG. 1, FIG. 2, FIG. 5, FIG. 6). In particular, the conduit element 52 is arranged such that a working gas from the working gas source 50 is introducable through the conduit element 52 through the first opening 12 into the discharge space 10. In an embodiment, the working gas source 50 is connected to the flow controller 40 by means of a conduit element 52 and further the flow controller 40 is connected to the discharge space 10 by means of another conduit element 52 (FIG. 3, FIG. 4).

The flow controller 40 can be used to control the working gas volume flow 60 in the discharge space 10. In the first state, the flow controller 40 is arranged so that no working gas enters the discharge space 10 through the first opening 12 (FIGS. 1, 4, 5, 6). In the second state, working gas from the working gas source 50 can enter the discharge space 10 through the first opening 12. Working gas flows from the first opening 12 through the discharge space 10 toward the second opening 14 (FIGS. 2, FIG. 3). The flow controller 40 can be a piezo valve (FIG. 4).

A system 1 shown in FIG. 5 has a mixing arrangement 54, wherein the flow controller 40 has the mixing arrangement 54. Further, the system 1 has a further gas source 51. The further gas source 51 may be connected to the mixing arrangement 54. In particular, the mixing arrangement 54 is configured to mix the working gas from the working gas source 50 with a further gas from the further gas source 51, so that a gas mixture is formed. The flow controller is formed to ensure that the resulting gas mixture is supplied to the discharge space 10.

When an electromagnetic field is generated in the discharge space 10, a plasma 5 is generated in the discharge space 10 and ejected from the discharge space 10 through the working gas volume flow 60 in the form of a plasma jet 6 through the second opening 14 (FIG. 2, FIG. 3).

In an embodiment according to the invention, the flow controller 40 is controlled with the aid of an automatic control unit 70 (FIGS. 1, 2, 5, 6). In particular, the state of the flow controller 40 can be set with the aid of the automatic control unit 70, i.e. the automatic control unit 70 controls the flow controller 40 such that it is in the first state or in the second state. Thus, the automatic control unit 70 can be used to control whether or not a plasma jet exits the discharge space.

FIGS. 7-15 show embodiments according to the invention of a system 1 for generating and controlling a non-thermal atmospheric pressure plasma with a plurality of discharge spaces.

Figure 7:
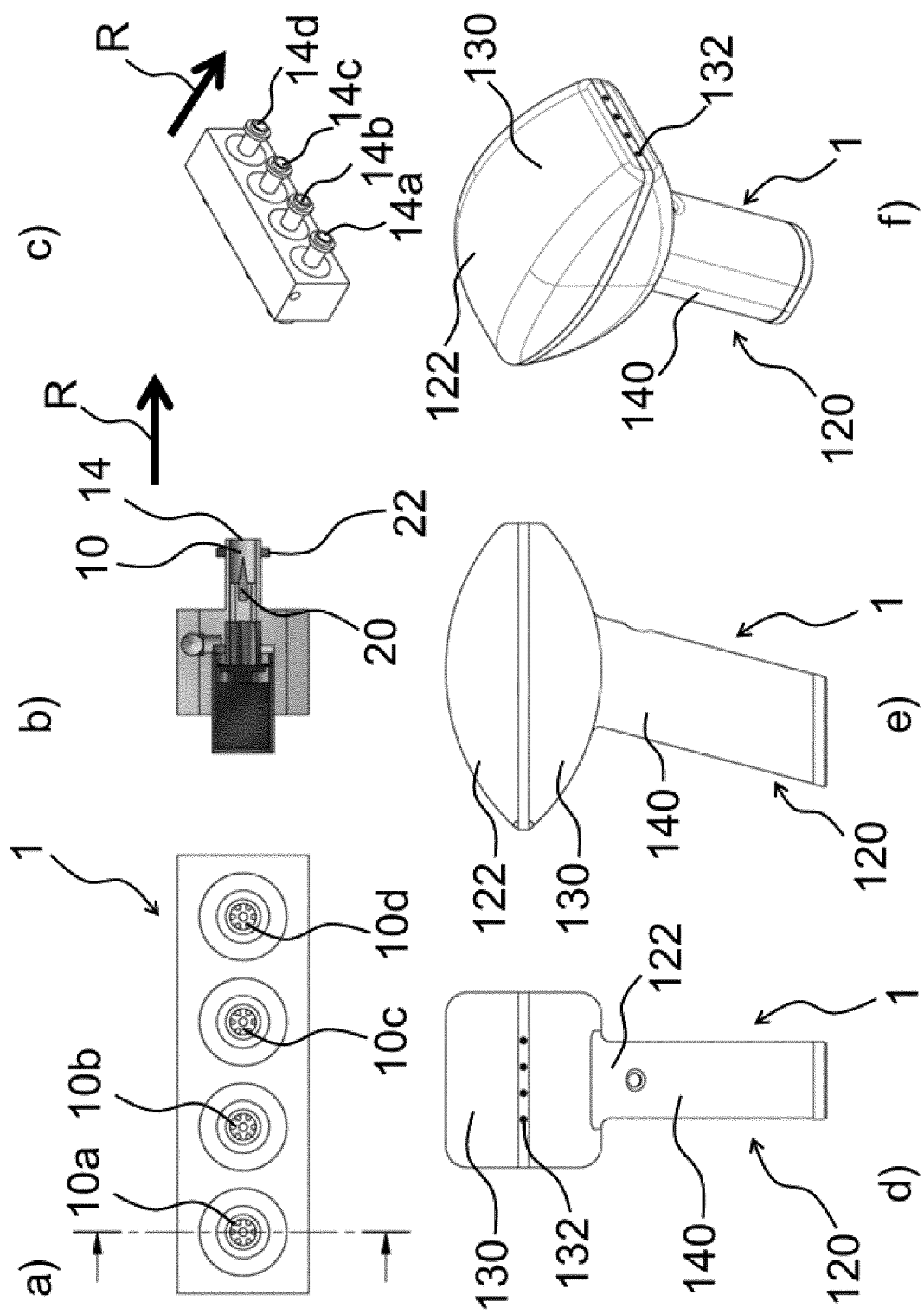

In FIG. 7 a)-f), an embodiment of the system 1 in the form of a handheld device 120 is shown in different perspectives. The illustrated handheld device 120 can be operated manually or robotically. FIGS. 7d)-f) show the handheld device 120 in a front view (d), a side view (e) as well as a perspective view (f). The handheld device 120 shown has a housing 122. The handheld device has a handle 140 as well as a headpiece 130. The headpiece 130 may have a plurality of recesses 132.

FIGS. 7 a)-c) show an arrangement of four discharge spaces 10a, 10b, 10c, 10d in a frontal view (a), a cross-sectional view (b) as well as a perspective view (c).

The four second openings 14a, 14b, 14c, 14d are arranged in a common plane. They point in a common direction R. The individual recesses 132 and the second openings 14a, 14b, 14c, 14d may be arranged relative to one another in such a way that a respective plasma jet of the respective second opening 14a, 14b, 14c, 14d can exit through the respective recess 132.

FIG. 8 to FIG. 12 show embodiments of a system 1 having a plurality of discharge spaces 10a, 10b, 10c. Each of the discharge spaces 10a, 10b, 10c shown have a respective first opening 12a, 12b, 12c and a respective second opening 14a, 14b, 14c. In each of the discharge spaces 10a, 10b, 10c a high voltage electrode 20a, 20b, 20c is arranged.

Figure 8:
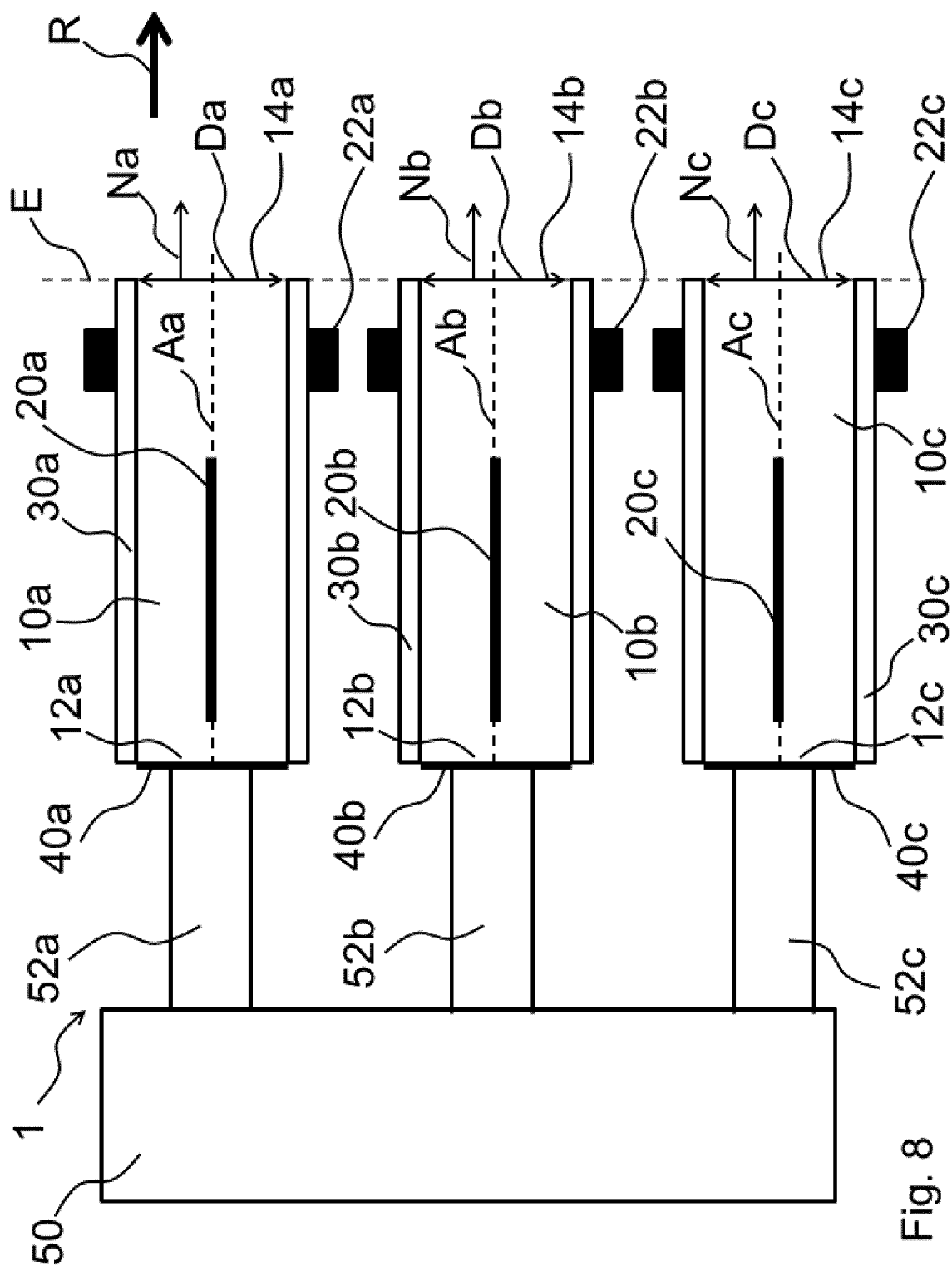

The longitudinal axes Aa, Ab, Ac of the respective discharge spaces 10a, 10b, 10c may be arranged parallel to each other (illustrated in FIG. 8).

The second openings 14a, 14b, 14c of the respective exemplary systems 1 shown (FIG. 8-FIG. 12) are arranged in a common plane E, respectively. The respective second openings 14a, 14b, 14c point in the same direction R. In particular, the surface normals Na, Nb, Nc point in the same direction R (FIG. 8, FIG. 11). The longitudinal axes Aa, Ab, Ac can extend in the direction of the surface normals Na, Nb, Nc.

Figure 9:
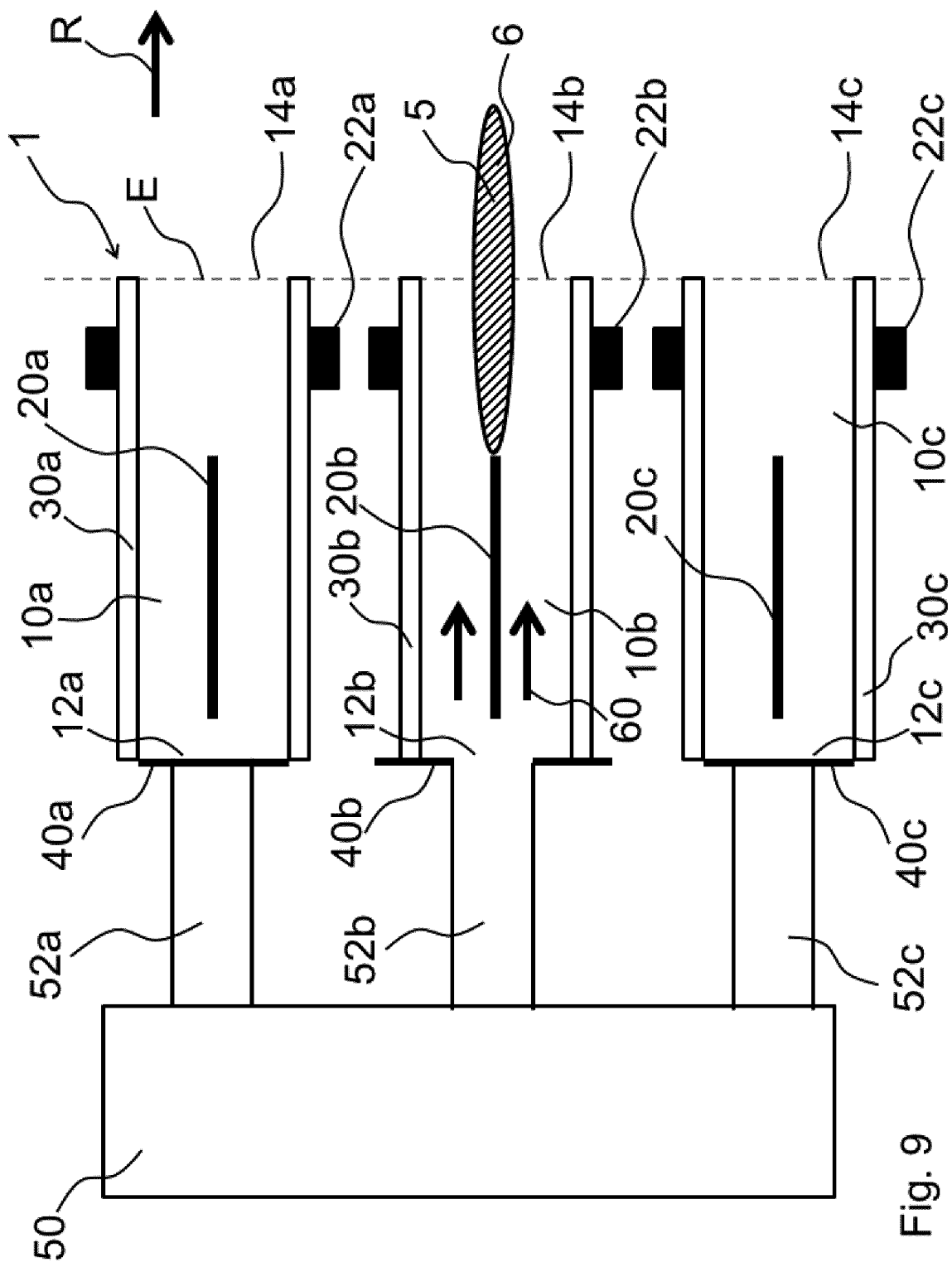

FIGS. 8 and 9 show a system 1 for generating and controlling a non-thermal atmospheric pressure plasma with three discharge spaces 10a, 10b, 10c. The discharge spaces 10a, 10b, 10c are connected to a common working gas source 50 via respective conduit elements 52a, 52b, 52c. The system 1 has flow controllers 40a, 40b, 40c, by means of which an introduction of a working gas from the working gas source 50 into a respective discharge space 10a, 10b, 10c is controlled.

The system 1 shown in FIGS. 8 and 9 comprises three discharge spaces 10a, 10b, 10c whose diameters Da, Db, Dc of the respective second openings 14a, 14b, 14c are identical (FIG. 8).

FIG. 8 shows an arrangement of the system 1 in which all three flow controllers 40a, 40b, 40c are in their first state. This means that in none of the three discharge spaces 10a, 10b, 10c working gas from the working gas source 50 is introduced through the respective first opening 12a, 12b, 12c.

FIG. 9 illustrates an arrangement in which a selected flow controller 40b is in its second state. The other two flow controllers 40a, 40c are in their respective first states. In this configuration, working gas is introduced into the selected discharge space 10b whose gas supply is controlled using the selected flow controller 40b. Plasma 5 is generated in the selected discharge space 10b and exits with the aid of the working gas volume flow 60 from the assigned second opening 14b as plasma jet 6.

Figure 10:
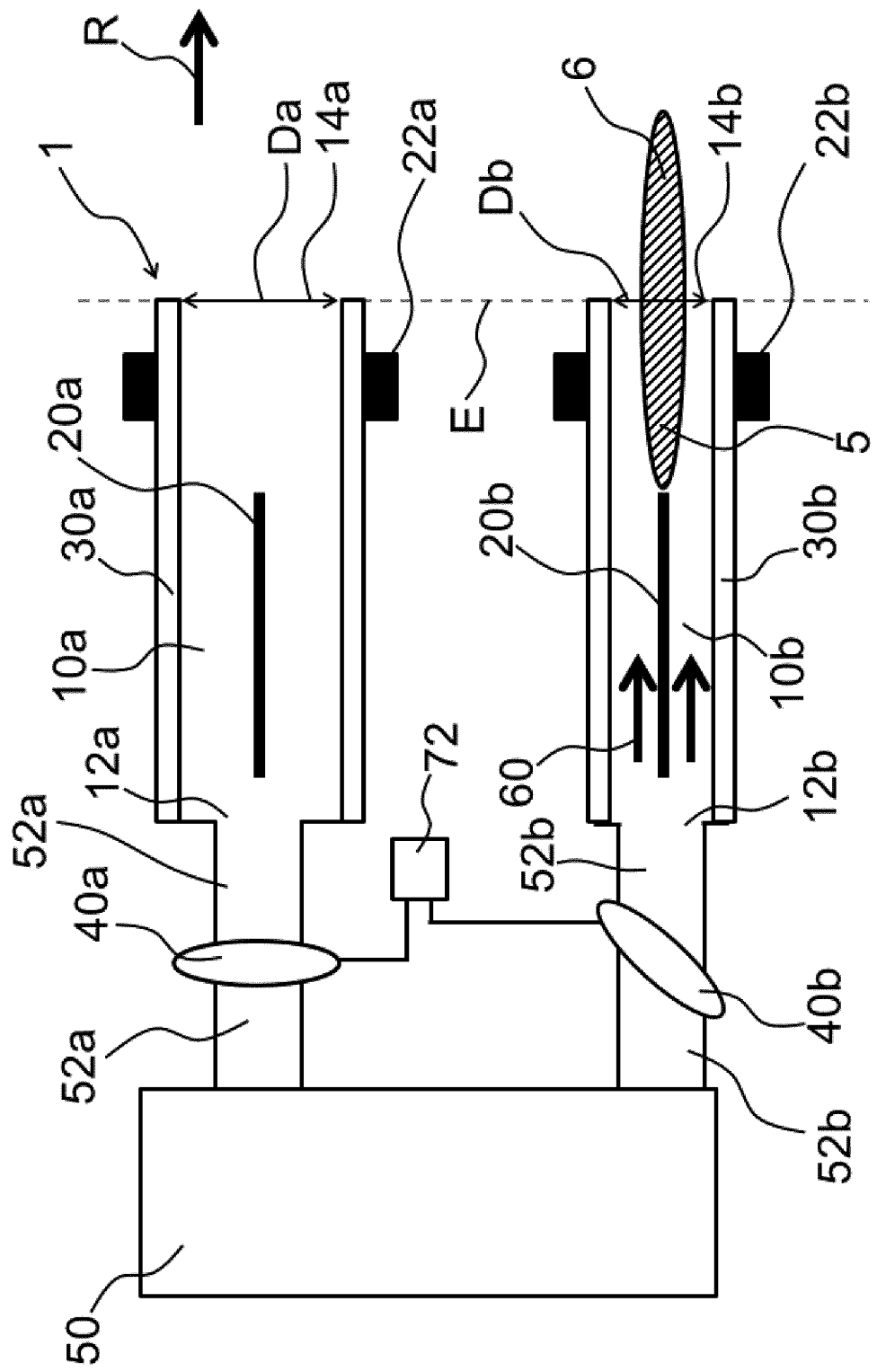
Figure 11:
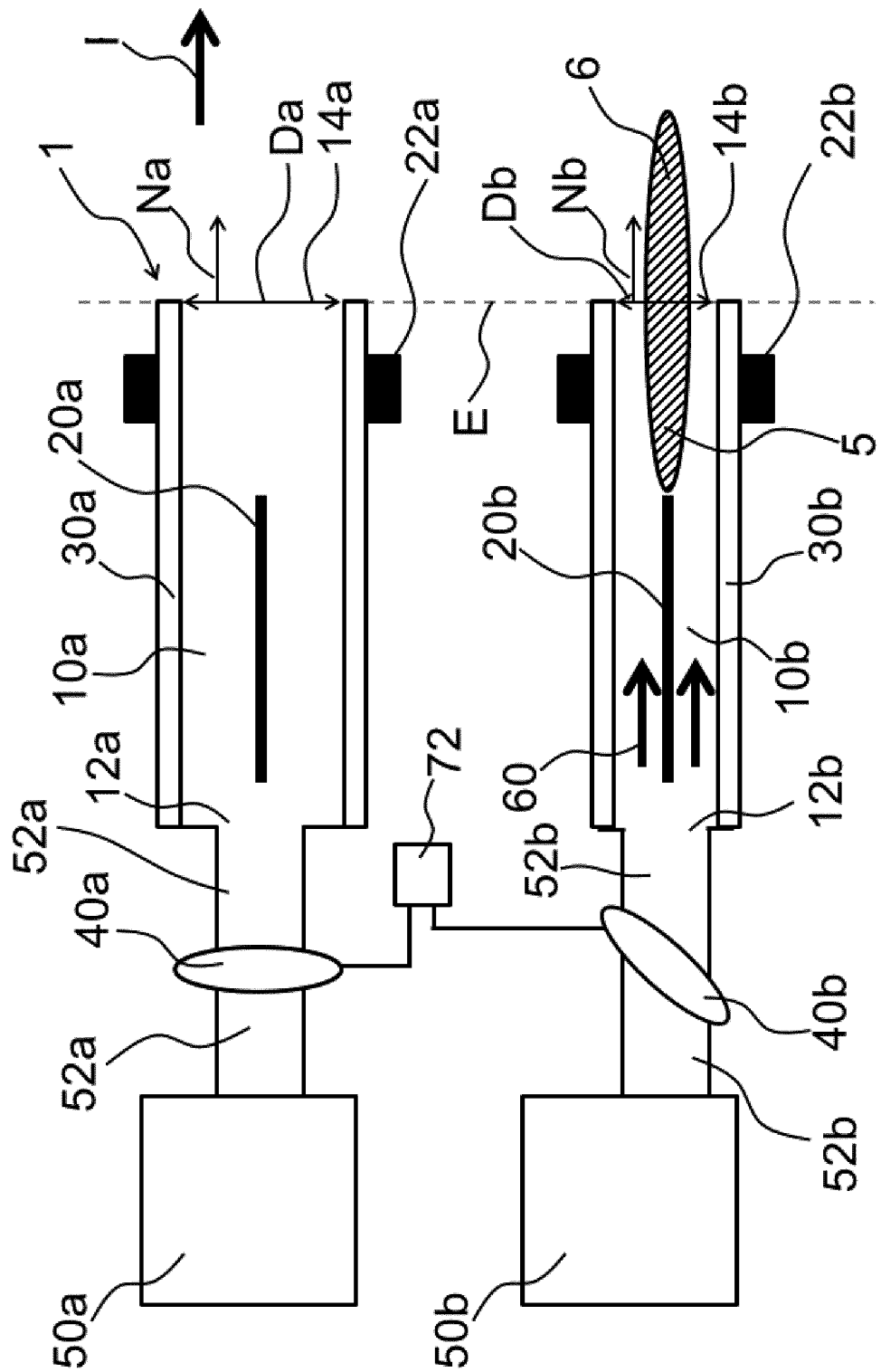
Figure 12:
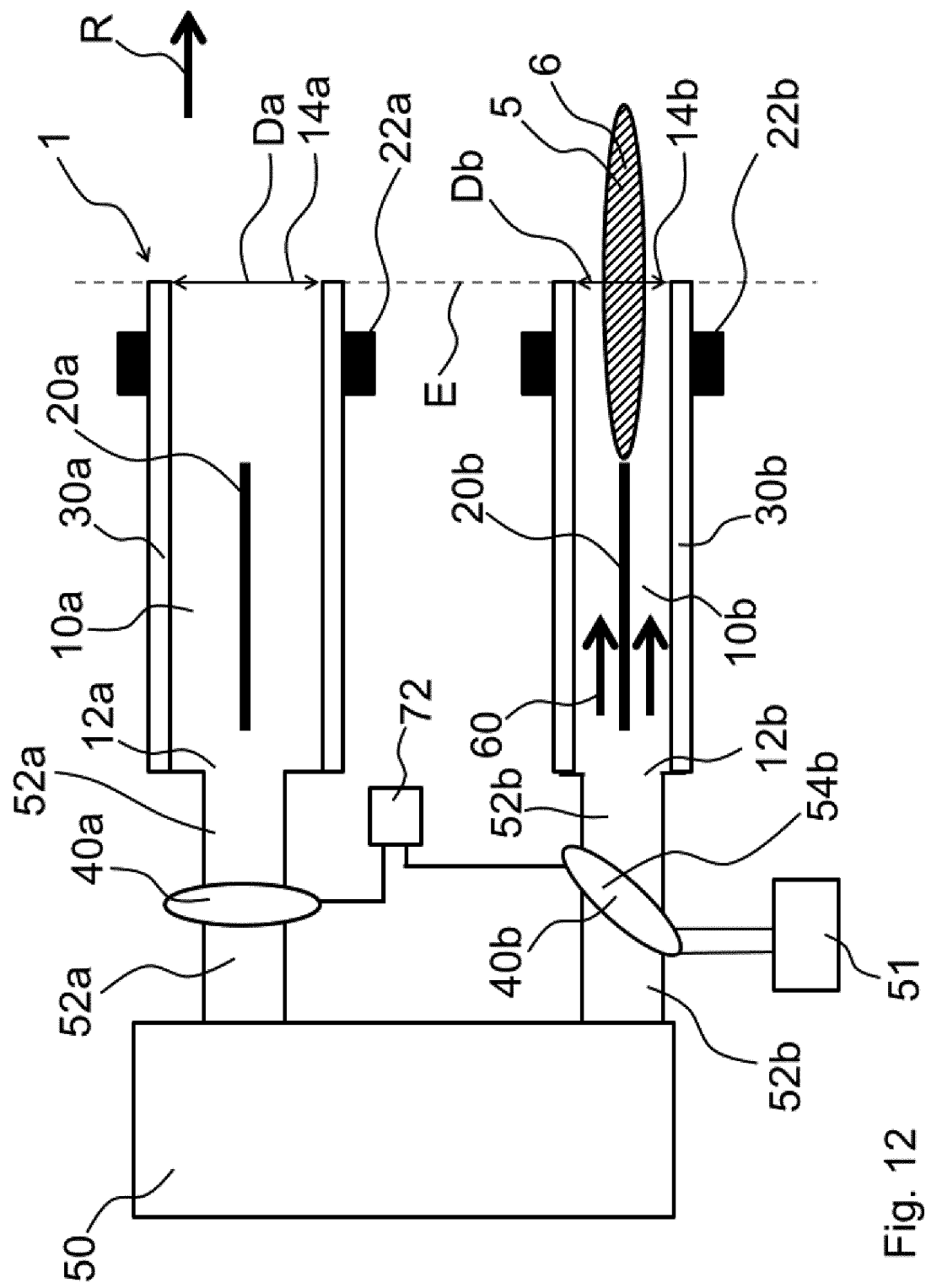

FIGS. 10-12 show a system 1 for generating and controlling a non-thermal atmospheric pressure plasma comprising two discharge spaces 10a, 10b, wherein the respective associated second openings 14a, 14b of the illustrated discharge spaces 10a, 10b have different diameters Da, Db FIG. 10 shows an arrangement of a system 1 in which a selected flow controller 40b is in the second state such that a plasma jet 6 exits from the second opening 14b of the respective discharge space 10b. The flow controllers 40a, 40b may both be connected to an automatic control system 72. The automatic control system 72 may control both flow controllers 40a, 40b. In particular, the automatic control system 72 controls such that a flow controller 40a, 40b is in the first state or in the second state.

FIG. 11 illustrates an arrangement in which the discharge spaces 10a, 10b are connected to different working gas sources 50a, 50b via the respective conduit elements 52a, 52b. That is, the system has a plurality of working gas sources 50a, 50b. The flow controllers 40a, 40b may be controlled by a common automatic control system 72.

In addition to a working gas source 50 connected to both discharge spaces 10a, 10b, the system 1 illustrated in FIG. 12 has another gas source 51. Further, the illustrated system 1 has a mixing arrangement 54b. The flow controller 40b may have the mixing arrangement 54b.

The further gas source 51 can be connected to the mixing arrangement 54b. With the aid of the mixing arrangement 54b, the working gas from the working gas source 50 is mixed with a further gas from the further gas source 51. This gas mixture is supplied to the discharge space 10b (by controlling the flow controller 40b).

Figure 13:
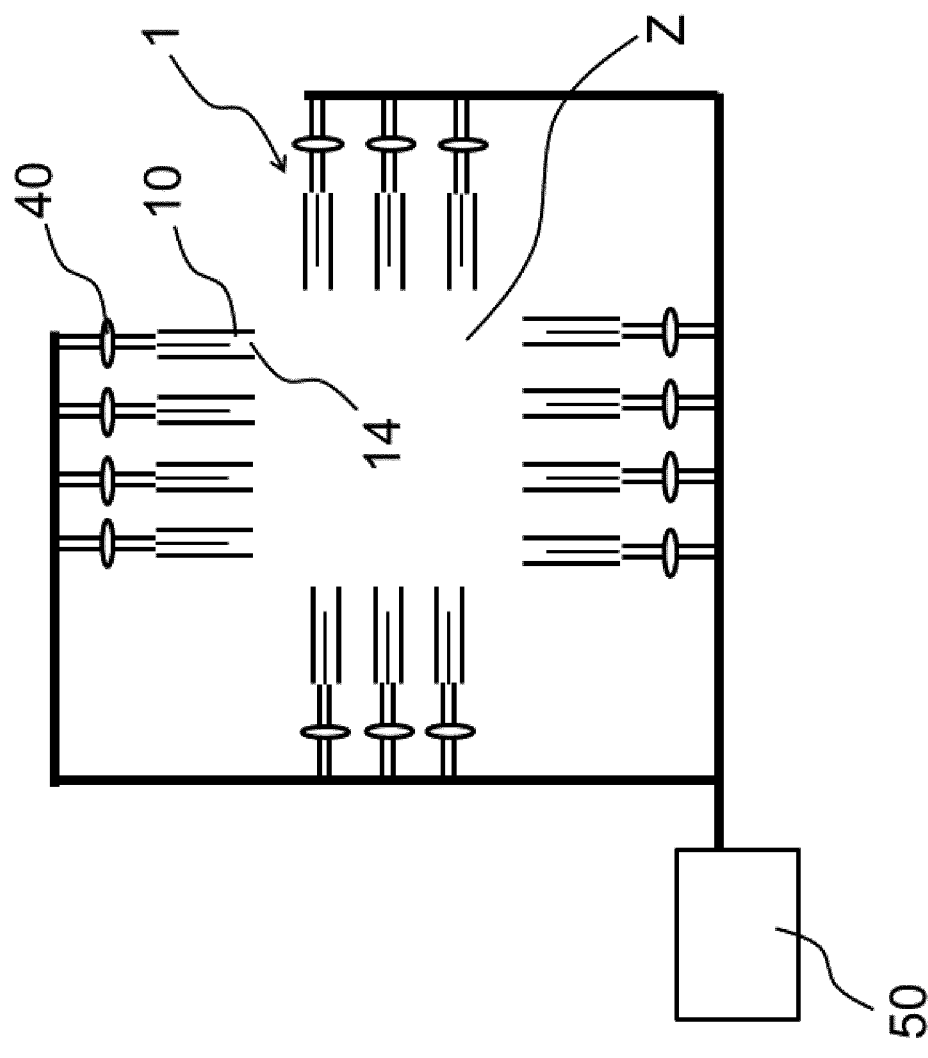
Figure 14:
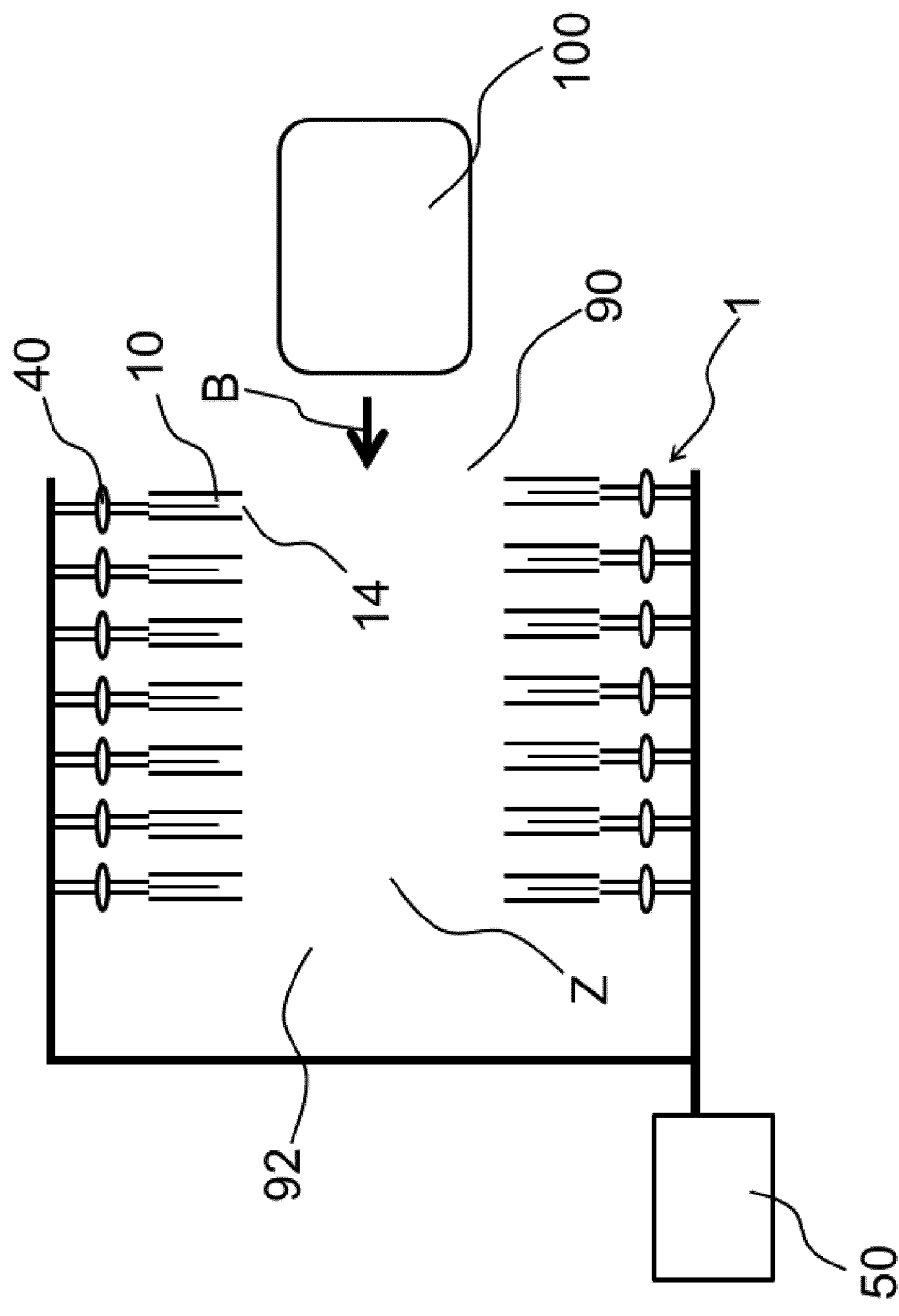
Figure 15:
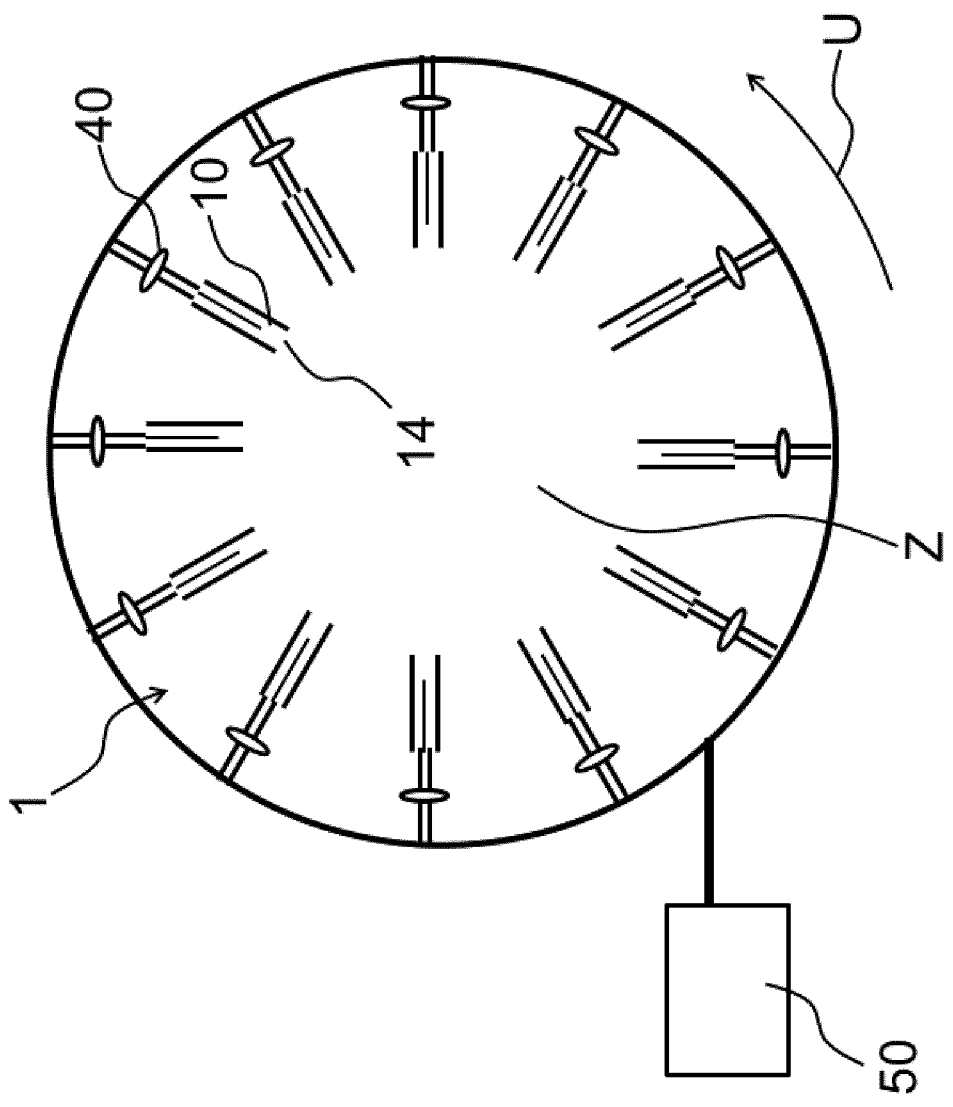

FIGS. 13, 14, and 15 show exemplary arrangements of the system 1 with a plurality of discharge spaces 10, wherein the second openings 14 of the discharge spaces 10 face a central region Z. The discharge spaces 10 are connected to a common working gas source 50. Using a plurality of flow controllers 40, the working gas flow in each of the discharge spaces 10 is independently controlled.

FIGS. 13 and 14 show a front view (FIG. 13) and a cross-sectional view (FIG. 14) of an exemplary arrangement in which the discharge spaces 10 are arranged at a cuboid volume.

The second openings 14 are oriented toward the cuboid. In an embodiment, the discharge spaces 10 are arranged at four faces of the cuboid (FIG. 13). No discharge spaces 10 are arranged at two opposing surfaces (FIG. 14). Through these created entrances 90, 92, an object 100 can be supplied to the central region Z along a direction of movement B (FIG. 14).

FIG. 15 illustrates an exemplary arrangement from the front, in which the discharge spaces 10 are arranged along a cylinder jacket. The second openings 14 face in the direction of the central region Z. The discharge spaces 10 can be arranged equidistantly to each other in the circumferential direction U.

The invention claimed is:

1. System (1) for generating and controlling a non-thermal atmospheric pressure plasma, wherein the system (1) comprising:
    a plurality of discharge spaces (10, 10a, 10b, 10c), wherein each discharge space (10, 10a, 10b, 10e) has:
        a respective first opening (12, 12a, 12b, 12c) capable of introducing a working gas into the respective discharge space (10, 10a, 10b, 10c),
        an assigned second opening (14, 14a, 14b, 14c) through which the plasma can exit the respective discharge space (10, 10a, 10b, 10c),
        at least one high-voltage electrode (20, 20a, 20b, 20c) for generating an electromagnetic field for generating a plasma (5) in the respective discharge space (10, 10a, 10b, 10e), so that in each discharge space (10, 10a, 10b, 10c), independently of the other discharge spaces (10, 10a, 10b, 10c), a plasma (5) is generatable,
    a plurality of flow controllers (40, 40a, 40b, 40c), each flow controller (40, 40a, 40b, 40c) being assigned to a respective discharge space (10, 10a, 10b, 10c) for controlling the plasma (5, 6) exiting through the assigned second opening (14, 14a, 14b, 14c), wherein each flow controller (40, 40a, 40b, 40c) is formed to:
        set a volume flow (60) of the working gas through the respective first opening (12, 12a, 12b, 12c) of the respective discharge space (10, 10a, 10b, 10c) from a working gas source (50, 50a, 50b) into the respective discharge space (10, 10a, 10b, 10c), and
        to adopt at least a first state and a second state, wherein in the first state no working gas from the working gas source (50, 50a, 50b) is supplied to the respective discharge space (10, 10a, 10b, 10c), so that in the respective discharge space (10, 10a, 10b, 10c), even with generated electromagnetic field in the respective discharge space (10, 10a, 10b, 10c), no plasma (5) exits from assigned second opening (14, 14a, 14b, 14c), and wherein in the second state the working gas from the working gas source (50, 50a, 50b) is supplied to the respective discharge space (10, 10a, 10b, 10c) and a plasma (5) is generated there, and the plasma (5, 6) exits from the assigned second opening (14, 14a, 14b, 14c),
characterized in that the system (1) is configured to generate at least one of a capacitively-coupled, an inductively-coupled and a microwave-induced plasma in the working gas supplied through the first opening.

2. The system (1) according to claim 1, characterized in that at least one ground electrode (22, 22a, 22b, 22c) is assigned to each discharge space (10, 10a, 10b, 10c), wherein the at least one high-voltage electrode (20, 20a, 20b, 20c) and the at least one ground electrode (22, 22a, 22b, 22c) for generating an electromagnetic field for generating a plasma (5) are configured in the respective discharge space (10, 10a, 10b, 10c).

3. The system (1) according to claim 1, characterized in that the system (1) comprises an automatic control system (72) formed to independently control the plurality of flow controllers (40, 40a, 40b, 40c) of the system (1) such that the flow controllers (40, 40a, 40b, 40c) can independently adopt at least the first state or the second state such that plasma (5) is generated only in a selected discharge space (10, 10a, 10b, 10e) and exits only from the second opening (14, 14a, 14b, 14c) of the selected discharge space (10, 10a, 10b, 10c).

4. The system (1) according to claim 3, characterized in that the automatic control system (72) is formed to control the flow controllers (40, 40a, 40b, 40c) of the plurality of flow controllers (40, 40a, 40b, 40c) of the system (1) independently of each other so that one flow controller (40, 40a, 40b, 40c) of the plurality of flow controllers (40, 40a, 40b, 40c) adopts the second state for a first time period and all other flow controllers (40, 40a, 40b, 40c) of the plurality of flow controllers (40, 40a, 40b, 40c) adopt the first state, and after the first time period, the flow controller (40, 40a, 40b, 40c) of the plurality of flow controllers (40, 40a, 40b, 40c) adopts the first state, wherein another flow controller (40, 40a, 40b, 40c) of the plurality of flow controllers (40, 40a, 40b, 40c) adopts the second state for a second time period, wherein the first and second time periods are consecutive or temporarily overlap.

5. The system (1) according to claim 1, characterized in that the system (1) is formed such that each discharge space (10, 10a, 10b, 10c) of the plurality of discharge spaces (10, 10a, 10b, 10c) is connectable or connected to a common working gas source (50), or wherein the system (1) is formed such that at least one discharge space (10, 10a, 10b, 10c) of the plurality of discharge spaces (10, 10a, 10b, 10c) is connectable or connected to its own working gas source (50a, 50b).

6. The system (1) according to claim 1, characterized in that the second openings (14, 14a, 14b, 14c) of the plurality of discharge spaces (10, 10a, 10b, 10c) face in the same direction (R), or that the second openings (14, 14a, 14b, 14c) of the plurality of discharge spaces (10, 10a, 10b, 10e) are positioned or positionable to face a central region (Z).

7. The system (1) according to claim 1, characterized in that the at least one flow controller (40, 40a, 40b, 40c) is continuously controllable so that the volume flow (60) through each discharge space (10, 10a, 10b, 10c) is continuously and individually settable.

8. The system (1) according to claim 1, characterized in that the at least one flow controller (40, 40a, 40b, 40c) is a proportional valve.

9. The system (1) according to claim 1, characterized in that the system (1) is configured to modulate the volume flow (60) of the working gas in each discharge space (10, 10a, 10b, 10c) by means of the flow controller (40, 40a, 40b, 40c), wherein the modulation of the volume flow (60) comprises more than two modulation states, in particular wherein the modulation of the volume flow (60) is continuously settable.

10. The system (1) according to claim 1, characterized in that each flow controller (40, 40a, 40b, 40c) is configured to have a control time between 0.1 ms and 1 s so that the volume flow (60) can be modulated with a respective time resolution.

11. The system (1) according to claim 1, characterized in that the system (1) has for each discharge space (10, 10*a*, 10*b*, 10*c*) at least one assigned sensor which detects a plasma parameter and which is configured to output a sensor signal indicative of the plasma parameter, wherein the system is configured to control the at least one flow controller (40, 40*a*, 40*b*, 40*c*) on the basis of the sensor signal in such a way that a plasma parameter to be achieved for the respectively assigned discharge space (10, 10*a*, 10*b*, 10*c*) is set.

12. The system (1) according to claim 1, characterized in that the system (1) has exactly one high-voltage electrode per discharge space (10, 10*a*, 10*b*, 10*c*) and no more than two ground electrodes.

13. The system according to claim 1, characterized in that each discharge space has exactly two openings-the first opening and the second opening.

14. A method for generating and controlling a non-thermal atmospheric pressure plasma utilizing a system (1) according to claim 1, comprising the steps:

generating an electromagnetic field in each discharge space (10, 10*a*, 10*b*, 10*c*) of the plurality of discharge spaces (10, 10*a*, 10*b*, 10*c*), setting each flow controller (40, 40*a*, 40*b*, 40*c*) of the plurality of flow controller (40, 40*a*, 40*b*, 40*c*) to a first state or a second state, wherein in the first state no working gas from the working gas source (50, 50*a*, 50*b*) is supplied to the respective discharge space (10, 10*a*, 10*b*, 10*c*) of the plurality of discharge spaces (10, 10*a*, 10*b*, 10*c*), so that in the respective discharge space (10, 10*a*, 10*b*, 10*c*) of the plurality of discharge spaces (10, 10*a*, 10*b*, 10*c*), even with generated electromagnetic field in the respective discharge space (10, 10*a*, 10*b*, 10*c*) of the plurality of discharge spaces (10, 10*a*, 10*b*, 10*c*), no plasma exits from the respective discharge space (10, 10*a*, 10*b*, 10*c*), and wherein, in the second state, the working gas from the working gas source (50, 50*a*, 50*b*) is supplied to the respective discharge space (10, 10*a*, 10*b*, 10*e*) of the plurality of discharge spaces (10, 10*a*, 10*b*, 10*c*), a plasma (5) is generated in the respective discharge space (10, 10*a*, 10*b*, 10*c*) of the plurality of discharge spaces (10, 10*a*, 10*b*, 10*c*), and the plasma (5, 6) exits from the assigned second opening (14, 14*a*, 14*b*, 14*c*).

\* \* \* \* \*